United States Patent [19]

Christensen et al.

[11] Patent Number: 4,745,188

[45] Date of Patent: * May 17, 1988

[54] PROCESS FOR PREPARING 3-SUBSTITUTED-6-SUBSTITUTED-7-OXO-1-AZABICYCLO[3.2.0]HEPT-2-ENE-2-CARBOXYLIC ACID

[75] Inventors: Burton G. Christensen, Scotch Plains; Ronald W. Ratcliffe, Matawan, both of N.J.

[73] Assignee: Merck & Co., Inc., Rahway, N.J.

[*] Notice: The portion of the term of this patent subsequent to Apr. 19, 2005 has been disclaimed.

[21] Appl. No.: 759,721

[22] Filed: Jul. 29, 1985

Related U.S. Application Data

[63] Continuation of Ser. No. 209,237, Nov. 21, 1980, which is a continuation-in-part of Ser. No. 141,020, Apr. 17, 1980, abandoned, which is a continuation of Ser. No. 061,738, Jul. 30, 1979, abandoned, which is a continuation of Ser. No. 843,478, Oct. 19, 1977, abandoned.

[51] Int. Cl.[4] ............... C07D 487/04; A61K 31/40
[52] U.S. Cl. ..................... 540/350; 540/310
[58] Field of Search ............. 514/210; 260/245.2 T; 540/350

[56] References Cited

U.S. PATENT DOCUMENTS 3,992,377 11/1976 Chauvette ............ 260/245.2 R
4,256,739 3/1981 Woodward et al. ...... 260/245.2 R

OTHER PUBLICATIONS

Scartazzini et al., Helvetica Chemica Acta, 58(8), 1975, pp. 2437–2450.

*Primary Examiner*—Nicholas S. Rizzo
*Attorney, Agent, or Firm*—Raymond M. Speer; Hesna J. Pfeiffer

[57] ABSTRACT

Disclosed is a process for preparing 3- and 6-substituted-7-oxo-1-azabicyclo[3.2.0]hept-2-ene-2-carboxylic acids:

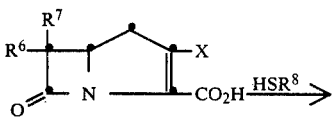

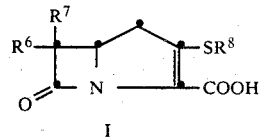

wherein: X is a leaving group such as chloro, bromo, tosyl, mesyl or the like; and $R^6$, $R^7$ and $R^8$ are, inter alia, independently selected from the group consisting of hydrogen, alkyl, alkenyl, aryl and aralkyl. Such compounds (I), as well as their pharmaceutically acceptable salt, ester and amide derivatives, are useful as antibiotics.

3 Claims, No Drawings

PROCESS FOR PREPARING 3-SUBSTITUTED-6-SUBSTITUTED-7-OXO-1-AZABICYCLO[3.2.0]HEPT-2-ENE-2-CARBOXYLIC ACID

This is a continuation of application Ser. No. 209,237 filed Nov. 21, 1980 which is a continuation-in-part of Ser. No. 141,020 filed Apr. 17, 1980, now abandoned, which is a continuation of Ser. No. 061,738 filed July 30, 1979, now abandoned, which in turn is a continuation of Ser. No. 843,478 filed Oct. 19, 1977, now abandoned.

BACKGROUND OF THE INVENTION

This invention relates to a process for preparing 3- and 6-substituted-7-oxo-1-azabicyclo[3.2.0]hept-2-ene-2-carboxylic acids and derivatives thereof which are useful as antibiotics:

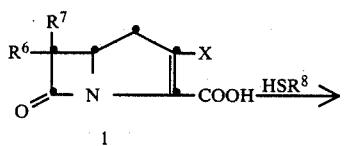

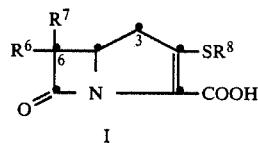

wherein X is a leaving group such as chloro, bromo, tosyl, mesyl, or the like; and wherein $R^6$, $R^7$, and $R^8$ are independently selected from the group consisting of hydrogen, substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the linear chain has 1–6 carbon atoms; heteroaryl, heteroaralkyl, heterocyclyl and heterocyclylalkyl wherein the substituent or substituents relative to the above-named radicals are selected from the group consisting of: amino, mono, di- and trialkylamino, hydroxyl, alkoxy, mercapto, alkylthio, arylthio such as phenylthio, sulfamoyl, amidino, guanidino, nitro, chloro, bromo, fluoro, cyano and carboxy; and wherein the hetero atom or atoms in the above-named heterocyclic moieties are selected from the group consisting of 1–4 oxygen, nitrogen or sulphur atoms; and wherein the alkyl moieties of the above-recited substituents have 1–6 carbon atoms.

This invention also relates to the carboxyl derivatives of I which are antibiotics and which may be represented by the following generic structure (I):

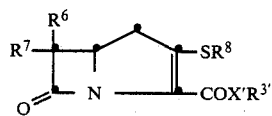

werein X' is oxygen, sulphur or NR' (R'=H or lower alkyl having 1–6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^{3'}$ is given in greater detail below.

There is a continuing need for new antibiotics, for unfortunately there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a process for preparing antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli, Proteus morganii,* Serratia, Pseudomonas and Klebsiella.

DETAILED DESCRIPTION OF THE INVENTION

The process of the present invention may be illustrated by the following scheme:

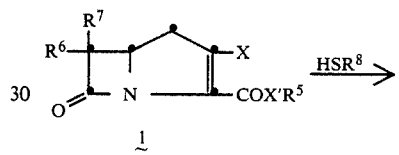

In words, the starting material 1 in a solvent such as dioxane, dimethylformamide (DMF), dimethylsulfoxide (DMSO), or the like is treated with a stoichiometric to 3 fold excess of the mercaptan reagent $HSR^8$ in the presence of a base such as $NaHCO_3$, NaH, triethylamine ($Et_3N$), diisopropylethylamine (i-$Pr_2NEt$) or the like at a temperature of from $-40°$ to 25° C. for from 1 to 6 hours. For free acid embodiments of I (X' is O and $R^5$ is H) the starting material 1 is taken such as X' is O and $R^5$ is a carboxyl blocking group which may be de-blocked by conventional procedures such as hydrolysis or hydrogenation after the above reaction with $HSR^8$. Free acid embodiments are also obtained by operating upon unprotected 1 (X'=O; $R^5$=H). Preferred blocking groups $R^5$ for deblocking by hydrogenation are benzyl, p-nitrobenzyl, o-nitrobenzyl or the like.

Starting material 1 is disclosed and claimed in copending, commonly assigned U.S. patent application Ser. No. 160,719 filed June 18, 1980. This application is incorporated herein by reference since it discloses the starting material 1 for practice of the present invention. The leaving group X on starting material 1 is preferably chloro, bromo, methylsulfonyloxy(mesyl), p-tolylsulfonyloxy (tosyl), or the like. The values of $R^6$, $R^7$, X' and $R^5$ which are common to final product I are defined below.

Final product I is disclosed and claimed in co-pending, commonly assigned U.S. patent application Ser.

No. 134,381 filed Mar. 27, 1980 now abandoned. This application is incorporated herein by reference since it discloses the final products which are made available by practice of the present invention.

Final products I are also disclosed in co-pending commonly assigned U.S. patent application Ser. No. 197,856, filed Oct. 17, 1980, now abandoned. This application is incorporated herein by reference since it idscloses the final antibiotic products which are made available by practice of the present invention.

1. Aliphatic Mercaptans:

$HSR^8$ wherein $R^8$ is 1-10 carbon alkyl, cycloalkyl, alkenyl, cycloalkenyl, or alkynyl; $R^8$ may be branched or unbranched, Examples

HSCH₃   HSCH₂CH₃

HSCH₂CH₂CH₃   HSCH(CH₃)₂

HS(CH₂)₃CH₃   
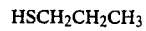

HSCH₂CH(CH₃)₂   

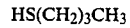   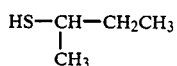

   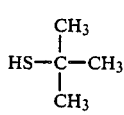

   

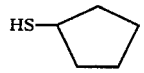   HS—CH₂—CH=CH₂

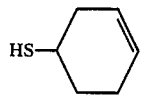

HS—CH₂—CH=C(CH₃)₂   HS—CH₂—C≡CH

HS—CH₂—C≡C—CH₃

2. Substituted Aliphatic Mercaptans:

$HSR^8$ wherein $R^8$ is a 1-10 carbon branched or unbranched alkyl, cycloalkyl, alkenyl, cycloalkenyl, or alkynyl group substituted by one or more halo, OH, $OR^1$, $\overset{O}{\underset{\|}{O C R^1}}$, $\overset{O}{\underset{\|}{O C N H_2}}$, $\overset{O}{\underset{\|}{O C N H R^1 R^2}}$, $NH_2$, $NHR^1$, $NR^1R^2$, $\overset{O}{\underset{\|}{CR^1}}$, $CO_2H$, $CO_2R^1$, $CONH_2$, $CONHR^1$, $CONHR^1R^2$, CN, $SR^1$, $\overset{O}{\underset{\|}{SR^1}}$, $SO_2R^1$, $SO_2NH_2$, $SO_2NHR^1$, $SO_2NR^1R^2$, $\overset{O}{\underset{\|}{NHCR^1}}$ $\overset{O}{\underset{\|}{NHCNH_2}}$, $\overset{O}{\underset{\|}{NHCNHR^1}}$, $\overset{O}{\underset{\|}{NHCNR^1R^2}}$, $\overset{O}{\underset{\|}{NHCOR^1}}$, wherein $R^1$ and $R^2$ are as previously defined relative to substituents on $R^8$. Preferred substituents are basic nitrogen-containing groups.

Examples $HS(CH_2)_nOR^1$    n = 2-4, $R^1 = H$, $\overset{O}{\underset{\|}{CCH_3}}$, $CH_3$ $HS(CH_2)_n\overset{O}{\underset{\|}{C}}XR$    n = 1-3, X = O, NH, $NR^1$;
$R^1 = H$, $CH_3$ $HS(CH_2)_nNH_2$    n = 2-4

$HS(CH_2)_nNHR^1$    n = 2-4,
$R^1 = CH_3$, $CH_2CH_3$,
$CH_2CH_2CH_3$, $\overset{O}{\underset{\|}{CCH_3}}$ $HS(CH_2)_nNR^1R^2$    n = 2-4,
$R^1/R^2 = CH_3$, $CH_2CH_3$

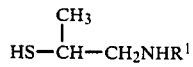    $R^1 = H$, $CH_3$, $\overset{O}{\underset{\|}{CCH_3}}$

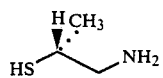    $R^1 = H$, $CH_3$

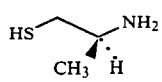

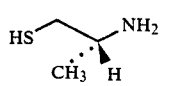

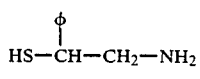

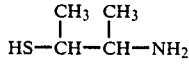

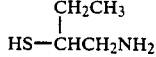

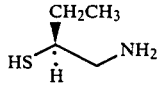

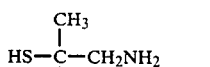

    $R^1 = H$, $CH_3$ $\overset{CH_3}{\underset{\underset{CH_3}{|}}{HS-CH_2-\overset{|}{C}-NH_2}}$

HS—CH₂CH₂SCH₃

-continued
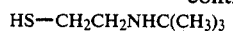
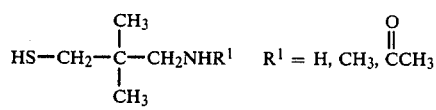 R¹ = H, CH₃, CCH₃
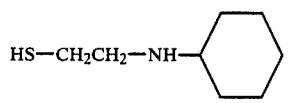
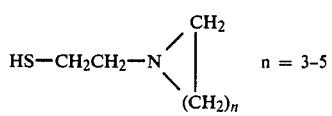 n = 3-5
 R¹ = H, CH₃; R² = H, CH₃
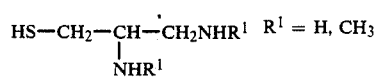 R¹ = H, CH₃
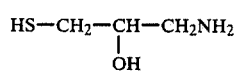
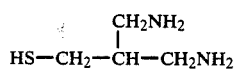
 R¹ = H, CH
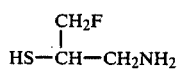
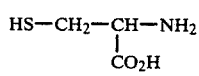
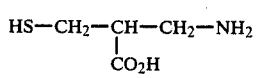
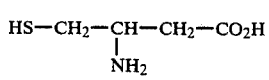
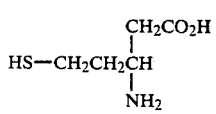
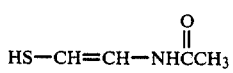
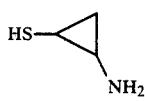
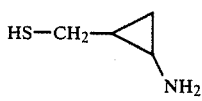
-continued
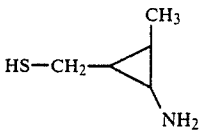
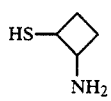
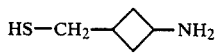
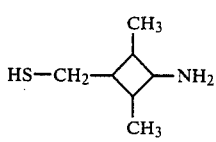
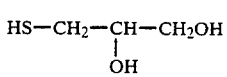
5-thio-D-glucose
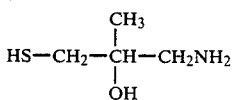
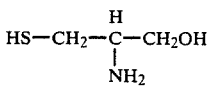
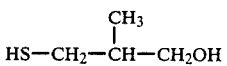
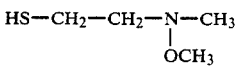
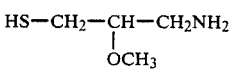
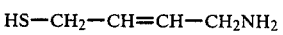
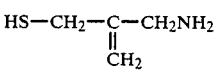
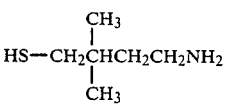
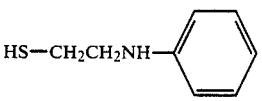
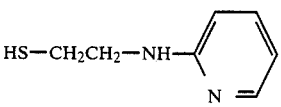

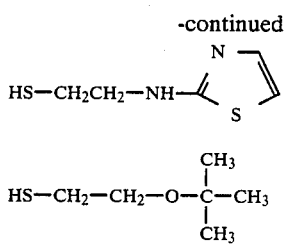

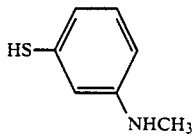

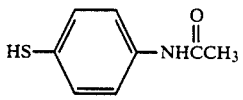

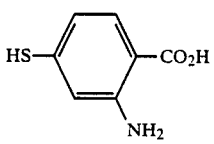

3. Aryl Mercaptans:

HSR$^8$ wherein R$^8$ is phenyl or substituted phenyl. The substituents are independently selected from those previously defined for R$^8$. Especially preferred substituents include alkyl, halo, hydroxy, alkoxy, acyloxy, acyl, carboxy, mercapto, sulfinyl, sulfonyl, amino, substituted amino, aminoalkyl, substituted aminoalkyl, amido, and ureido.

n = 1, 2 or 3,

X = F, Cl, Br, OH, OR, O$\overset{\overset{O}{\|}}{C}$R$^1$, NH$_2$,

NHR$^1$, NR$^1$R$^2$, CH$_2$NH$_2$, CH$_2$NR$^1$R$^2$, CO$_2$H,
CO$_2$R$^1$, COR$^1$, CONH$_2$, CONR$^1$R$^2$, R$^1$CONH,

R$^1$NHCONH, SR$^1$, $\overset{\overset{O}{\|}}{S}$R$^1$, SO$_2$R$^1$, CH$_3$, CF$_3$;

R$^1$ and R$^2$ are as previously defined under R$^8$.

Examples

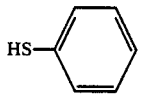

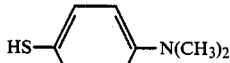

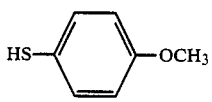

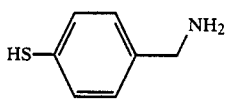

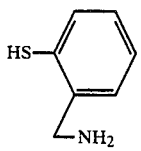

4. Heteroaryl Mercaptans:

HSR$^8$ wherein R$^8$ is a substituted or unsubstituted heteroaryl group containing 1-O, N or S atoms. Typical substituents include those mentioned above under "Aryl Mercaptans".

EXAMPLES

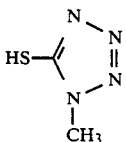

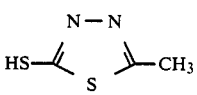

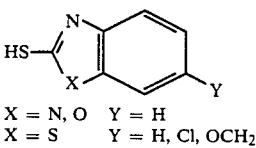

X = N, O    Y = H
X = S        Y = H, Cl, OCH$_2$CH$_3$

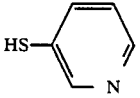

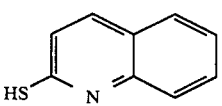

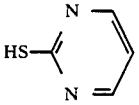

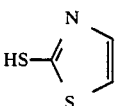

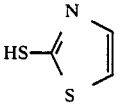

-continued

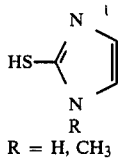
R = H, CH₃

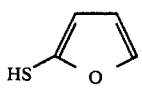

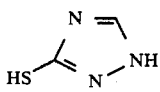

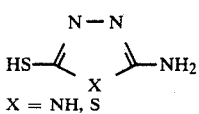
X = NH, S

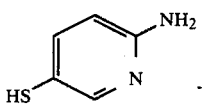

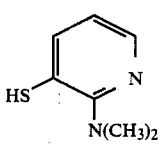

5. Arylaliphatic Mercaptans:

HSR⁸ where R⁸ is a 1-6 carbon branched or unbranched alkyl, cycloalkyl, alkenyl, or alkynyl group substituted by a phenyl or substituted phenyl group. Typical phenyl substituents include those mentioned under "Aryl Mercaptans".

Examples

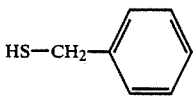

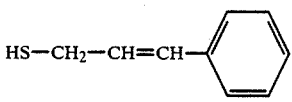

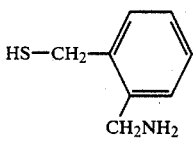

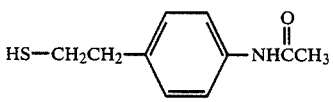

6. Heteroarylaliphatic and Heterocyclylaliphatic, and heterocyclic Mercaptans

HSR⁸ wherein R⁸ is a 1-6 carbon branched or unbranched alkyl, cycloalkyl, alkenyl, or alkynyl group substituted by a heteroaryl or heterocyclyl group containing 1-4, O, N, or S atoms. The heteroaryl or heterocyclic group is unsubstituted or substituted by those substituents mentioned under "Aryl Mercaptans", (No. 3 above).

Examples

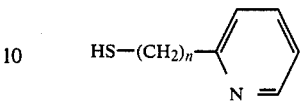

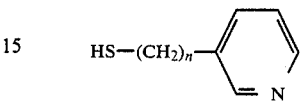

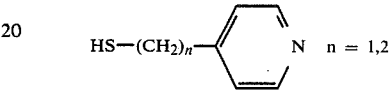
n = 1,2

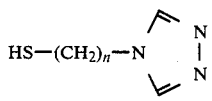

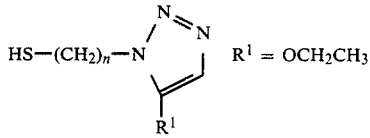
R¹ = OCH₂CH₃

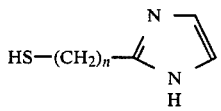

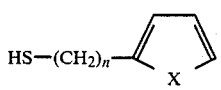

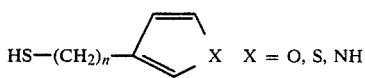
X = O, S, NH

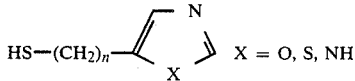
X = O, S, NH

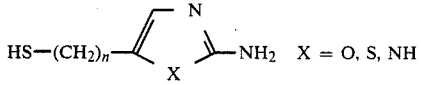
X = O, S, NH

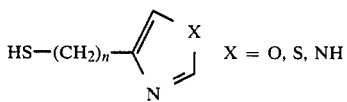
X = O, S, NH

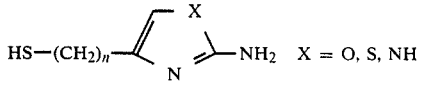
X = O, S, NH

-continued

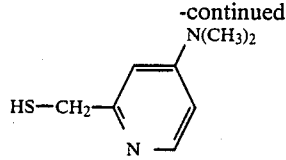

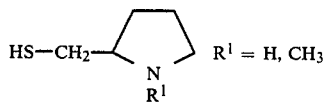  R¹ = H, CH₃

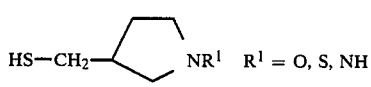  R¹ = O, S, NH

  X = O, NH, NCH₃

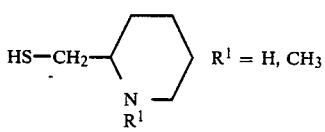  R¹ = H, CH₃

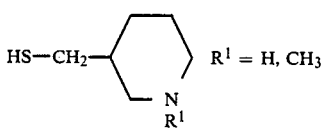  R¹ = H, CH₃

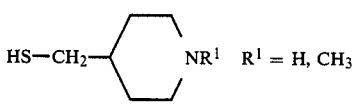  R¹ = H, CH₃

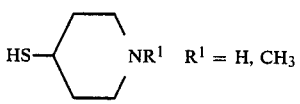  R¹ = H, CH₃

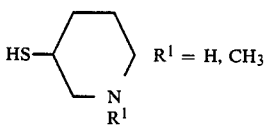  R¹ = H, CH₃

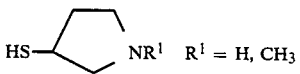  R¹ = H, CH₃

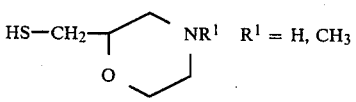  R¹ = H, CH₃

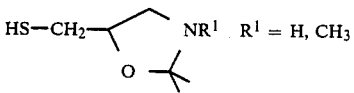  R¹ = H, CH₃

7. Alkyl-Heteroatom-Alkyl Mercaptans, HSR⁸ Wherein R⁸ is

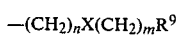

wherein n=2 to 4, m=2 to 4; X is NR°, O or S; and wherein R° is

H, CH₃, CH₂CH₃, CH₂CH₂OH, or CH₂CH₂NH₂ and

R⁹ is OH, NH₂, NHCH₃, N(CH₃)₂, OCCH₃, NHCCH₃.
                                    ‖          ‖
                                    O          O

Note, in the above representation, the methylene carbons may be branched; for example:

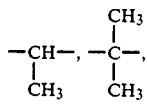

and the like.

The following HSR⁸ are representative of this class:

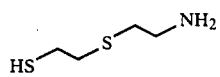

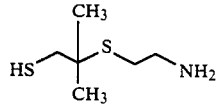

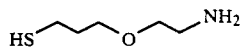

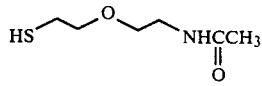

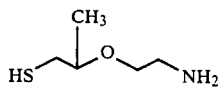

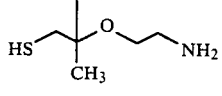

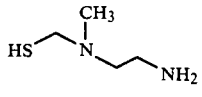

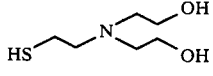

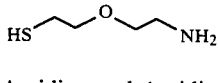

8. Amidino and Amidinium Mercaptans HSR⁸ Wherein R⁸ is:

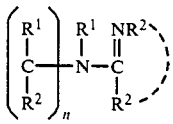

-continued

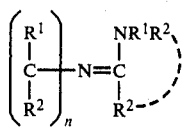

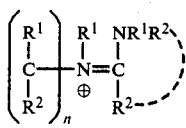

and wherein n=2-6; $R^1$ and $R^2$ are as initially defined under $R^8$; and the dotted line indicates provision for the ring formed by the joinder of substituents carried by the imino carbon atoms. Such amidino and amidinium embodiments of final products I are also conveniently obtained by N-derivatization of the corresponding amino embodiment Ia according to the procedure disclosed in U.S. Pat. No. 4,194,047 which patent is incoproated herein by reference since the N-derivatization of thienamycin disclosed in the incorporated by reference patent is strictly analogous to the N-derivatization contemplated to achieve the amidino embodiments characterized herein.

The following reaction summarizes such N-derivatization:

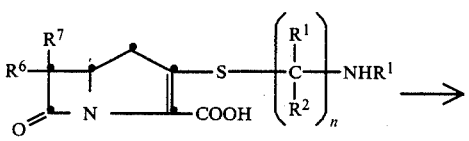

Ia

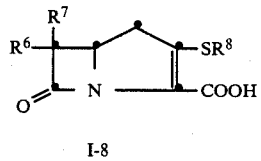

I-8 wherein: relative to I-8, $R^8$ is defined above in this category No. 8.

Relative to the amidino embodiments characterized under this heading, representatively preferred values for $R^1$ and $R^2$ attached to the carbon atom include:
H,
CH$_3$,
CH$_2$CH$_3$,
CH$_2$OH,
OCH$_3$,
CH$_2$NH$_2$,
F,
PHENYL,
CF$_3$,
CH(CH$_3$)$_2$,
CH$_2$CH$_2$CH$_3$,
CH$_2$F
benzyl, SCH$_3$, N(CH$_3$)$_2$, N$^+$(CH$_3$)$_3$X$^-$ (X$^-$ defined above)

Representatively preferred values for $R^1$ and $R^2$ attached to the nitrogen atoms include:
H, phenyl, CH(CH$_3$)$_2$, C(CH$_3$)$_3$, NH$_2$,
CH$_3$, NHCH$_3$, N(CH$_3$)$_2$,
CH$_2$CH$_3$,
CH$_2$CH$_2$OH,
—(CH$_2$)$_4$—,
—CH$_2$CH$_2$—O—CH$_2$CH$_2$,
OCH$_3$ Representatively preferred values for $R^2$ attached to the imino carbon atom include:
H,
CH$_3$,
CH$_2$CH$_3$,
phenyl The following values for HSR$^8$ are also classified under the amidino mercaptans, giving rise to amidino embodiments of I:
$R^8$ is:

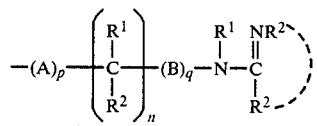

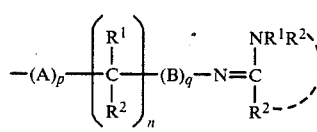

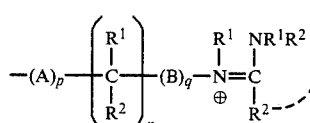

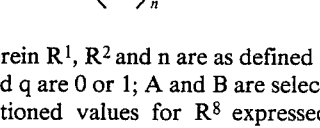

wherein $R^1$, $R^2$ and n are as defined immediately above; p and q are 0 or 1; A and B are selected from: the aforementioned values for $R^8$ expressed in bivalent form (—$R^8$—) from categories No.'s 1–7; thus, A and B (or —$R^8$—) are selected from: cycloalkyl, alkenyl, cycloalkenyl, alkynyl (see Class No. 1, above); substituted: cycloalkyl, alkenyl, cycloalkenyl, alkynyl (see Class No. 2, above); phenyl and substituted phenyl (see Class No. 3, above); substituted and unsubstituted heteroaryl (see Class No. 4, above); aryl aliphatic (see Class No. 5, above); heteroarylaliphatic, heterocyclylaliphatic, and heterocyclic (see Class No. 6, above); and alkylheteroatom-alkyl (see Class No. 7, above); and B can also be selected from —O— and —NR$^1$—.

Examples

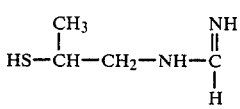

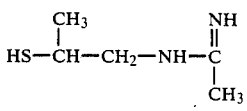

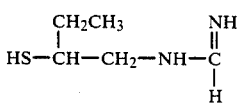

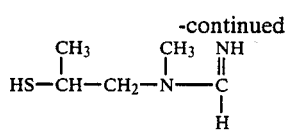
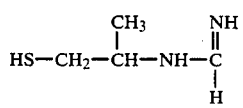
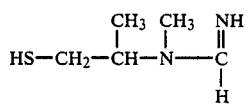
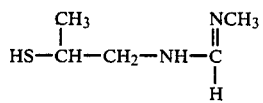
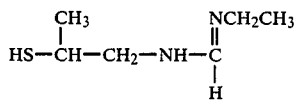
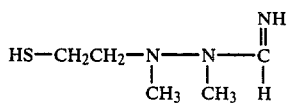
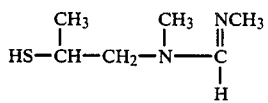
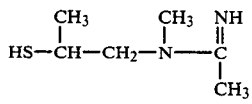
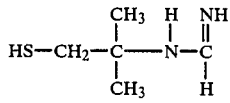
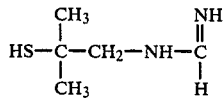
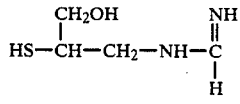
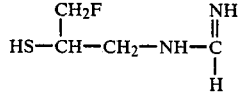
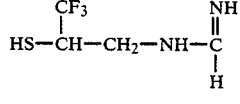
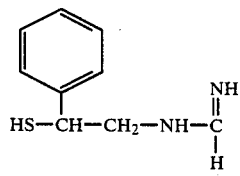
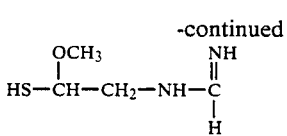
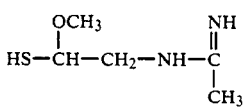
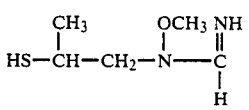
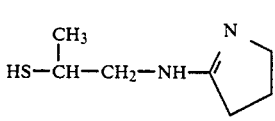
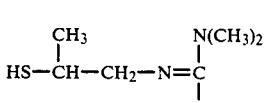
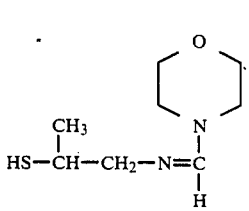
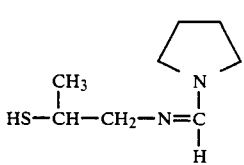
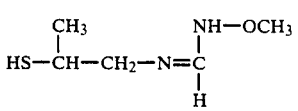
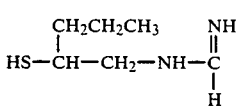
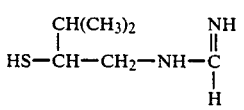
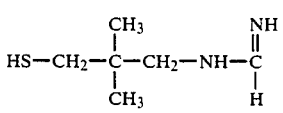
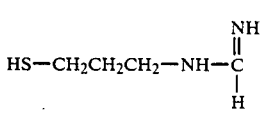
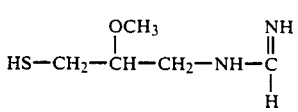

-continued

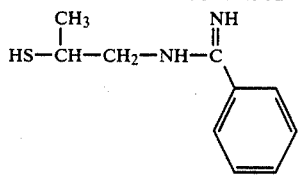
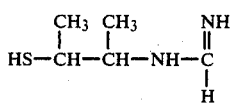
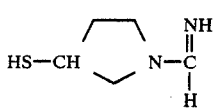
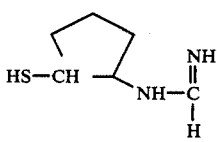
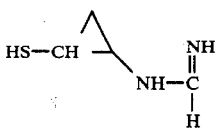
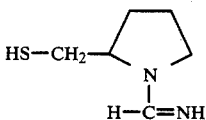
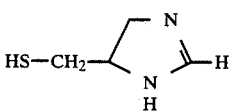
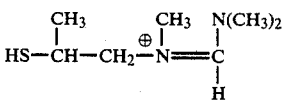
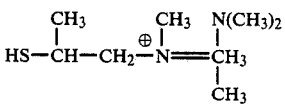
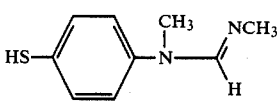
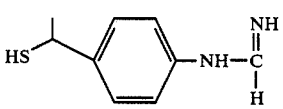
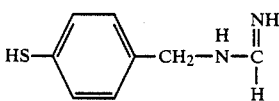

-continued

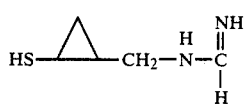
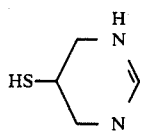
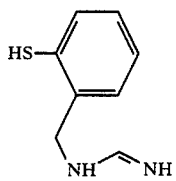

9. Guanidino and Guanidinium Mercaptans $HSR^8$ Wherein $R^8$ is:

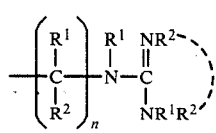
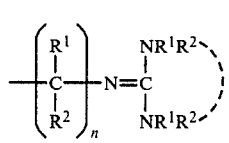
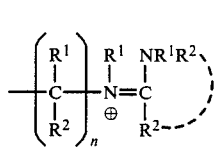

and wherein n=2-6; $R^1$ and $R^2$ are as initially defined under $R^8$; and the dotted line indicates provision for the ring formed by the joinder of substituents carried by the imino carbon atom. Such guanidino and guanidinium embodiments of the final products I are conveniently obtained by N-derivatization of the corresponding amino embodiments according to procedures disclosed in U.S. Pat. No. 4,194,047 as was explained under 8. above.

Such guanidino embodiments are also conveniently prepared directly following the procedure described in Diagram III, above. Such procedure is also disclosed in co-pending, concurrently filed, commonly assigned U.S. patent application Ser. No. 197,865 filed Oct. 17, 1980 of W. J. Leanza, now abandoned, which application is incorporated herein by reference.

Representatively preferred values for $R^1$ and $R^2$ attached to the carobn atom include:
H,
$CH_3$,
$CH_2CH_3$,
$CH_2OH$,
$OCH_3$,
$CH_2NH_2$,
F,
phenyl,
$CF_3$, CH(CH₃)₂,
CH₂CH₂CH₃,
CH₂F, benzyl, N(CH₃)₂

Representatively preferred values for $R^1$ and $R^2$ attached to nitrogen atoms include:
H,
CH₃,
CH₂CH₃,
CH₂CH₂OH,
—(CH₂)₂—
—(CH₂)₃—
CH(CH₃)₂
—(CH₂)₄—, phenyl, CH(CH₃)₂, C(CH₃)₃,
—CH₂CH₂OCH₂CH₂—
OCH₃, NH₂, NHCH₃, N(CH₃)₂

The following values for $HSR^8$ are also classified under the guanidino mercaptans, giving rise to the guanidino embodiments of I:

$R^8$ is:

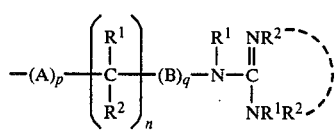

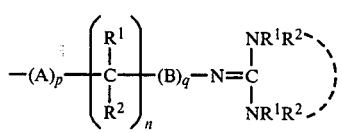

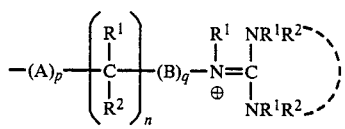

wherein $R^1$ and $R^2$ and n are as defined immediately above; p and q are 0 or 1; A and B are selected from: the aforementioned values for $R^8$ expressed in bivalent form from categories No.'s 1-7.

Thus, A and B (or —$R^8$— are selected from: cycloalkyl, alkenyl, cycloalkenyl, alkynyl (see Class No. 1, above); substituted: cycloalkyl, alkenyl, cycloalkenyl, alkynyl (see Class No. 2, above); phenyl and substitued phenyl (see Class No. 3, above); substituted and unsubstituted heteroaryl (see Class No. 4, above); aryl aliphatic (see Class No. 5, above); heteroarylaliphatic, heterocyclylaliphatic, and heterocyclic (see Class No. 6, above); and alkyl-heteroatom-alkyl (see Class No. 7, above); B is also selected from —O— and —NR'—.

Examples

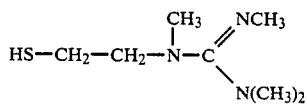

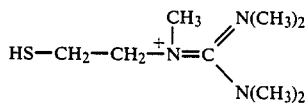

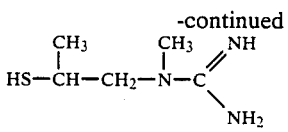

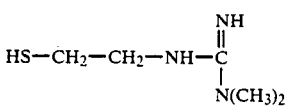

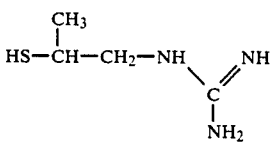

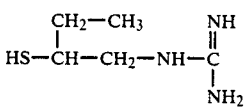

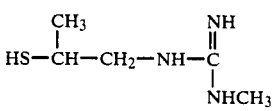

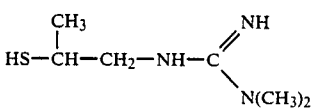

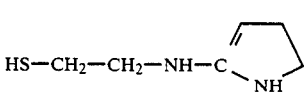

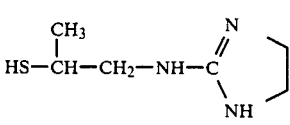

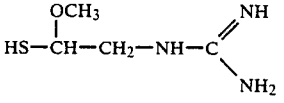

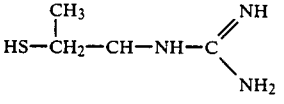

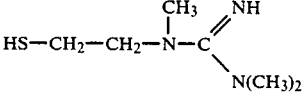

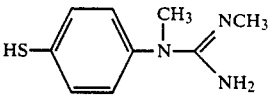

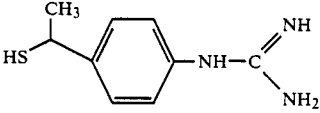

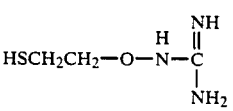

-continued

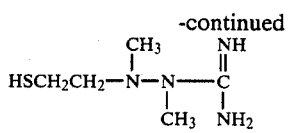

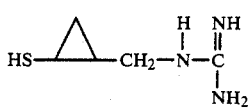

10. Carbamimidoyl and carbamimidinium Mercaptans HSR$^8$

Wherein R$^8$ is:

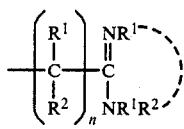

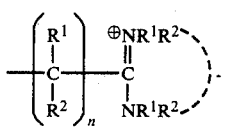

and wherein n is 0–6, and R$^1$ and R$^2$ are as initially defined under R$^8$; the two nitrogen atoms demonstrated in the above structure may be joined via their substituents to form a ring which is indicated by the dotted line.

Representatively preferred values for R$^1$ and R$^2$ attached to the carbon atom include: hydrogen, methyl, ethyl, propyl, isopropyl, phenyl, benzyl, amino, methylamino, dimethylamino, trimethyl ammonium, ethylthio, methoxy, methoximino, methylene, vinyl, hydroxy, fluoro, trifluoromethyl, hydroxymethyl, fluoromethyl. Representatively preferred values of R$^1$ and R$^2$ attached to nitrogen atoms include: hydrogen, ethyl, methyl, phenyl, benzyl, isopropyl, t-butyl, methoxy, amino, methylamino, dimethylamino, —(CH$_2$)$_4$—, —(CH$_2$)$_3$, —(CH$_2$)$_2$—.

The following values for HSR$^8$ are also classified under the carbamimidoyl mercaptans, giving rise to carbamimidoyl embodiments of I; R$^8$ is:

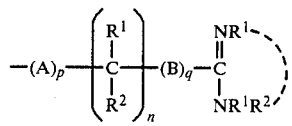

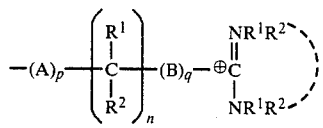

wherein R$^1$, R$^2$ and n are as defined immediately above; p and q are 0 or 1; and A and B are selected from the aforementioned values of R$^8$ expressed in bivalent form (e.g., —R$^8$—) from categories No.'s 1–7; thus, A and B (or —R$^8$—) are selected from: cycloalkyl, alkenyl, cycloalkenyl, alkynyl (see Class No. 1, above); substituted: cycloalkyl, alkenyl, cycloalkenyl, alkynyl (see Class No. 2, above); phenyl and substituted phenyl (see Class No. 3, above); substituted and unsubstituted heteroaryl (see Class No. 4, above); arylaliphatic (see Class No. 5, above); heteroarylaliphatic, heterocyclylaliphatic, and heterocyclic (see Class No. 6, above); and alkylheteroatom-alkyl (see Class No. 7, above).

Examples

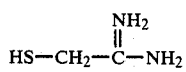

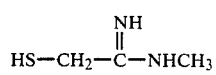

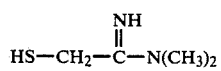

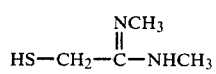

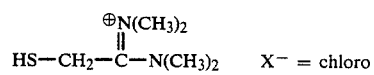 X$^-$ = chloro

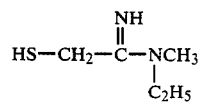

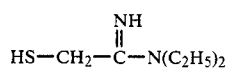

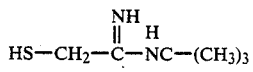

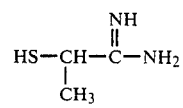

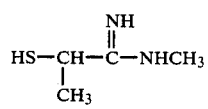

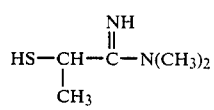

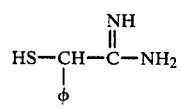

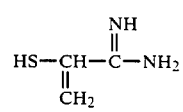

-continued
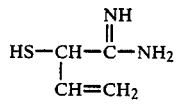
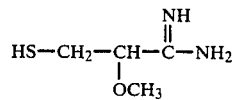
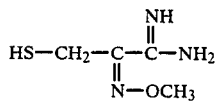
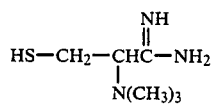
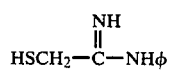
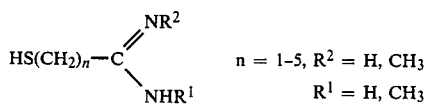
n = 1-5, R² = H, CH₃
R¹ = H, CH₃
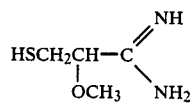
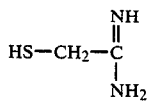
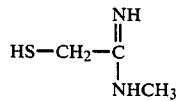
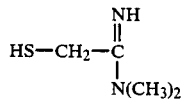
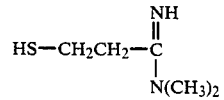
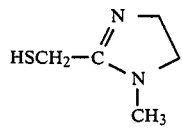
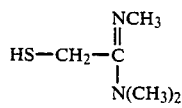
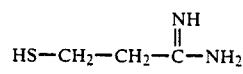
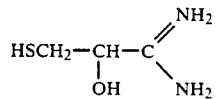
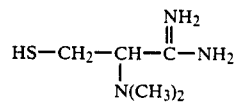
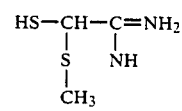
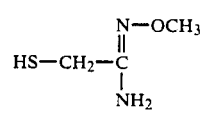
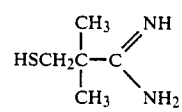
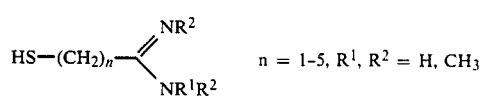
n = 1-5, R¹, R² = H, CH₃
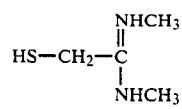
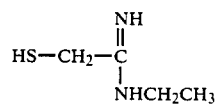
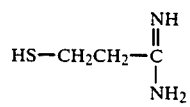
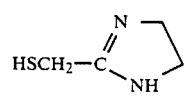
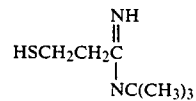
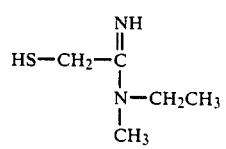

25
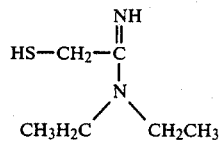
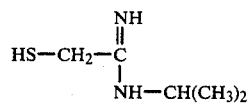
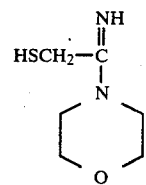
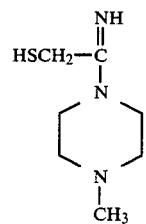
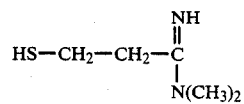
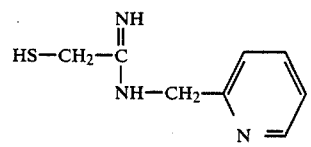
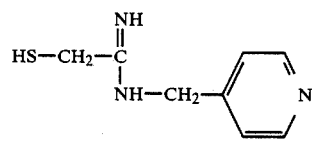
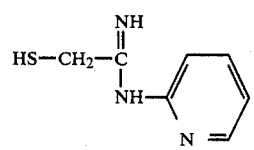
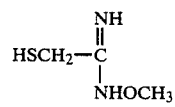
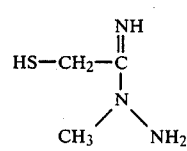
26
-continued
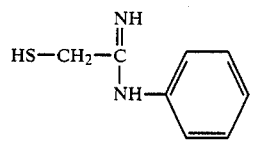
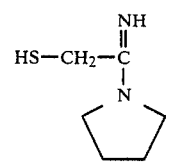
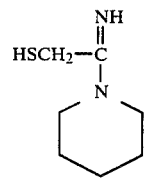
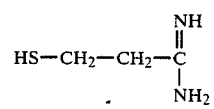
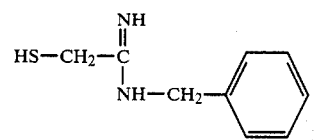
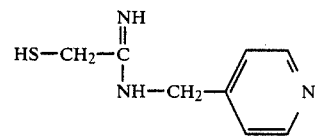
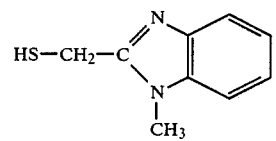
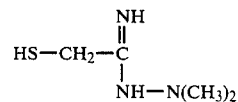
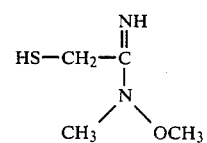
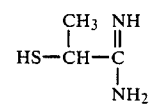

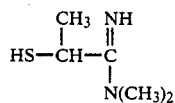
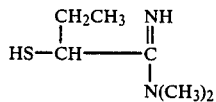
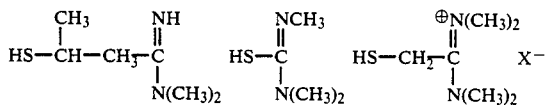
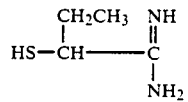
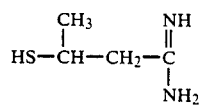
11. Multiple Iminomethyl Mercaptans HSR⁸
Wherein R⁸ is:
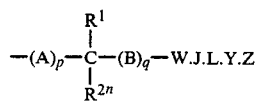
wherein W, J, L, Y and Z are chosen from
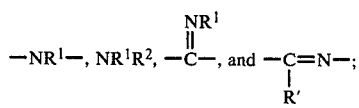
and R¹ is as previously, initially defined.
Representative combination of radicals W, J, L, Y & Z are:
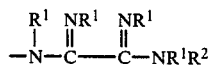
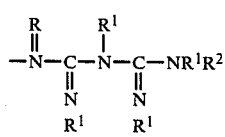
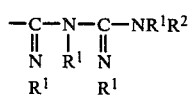
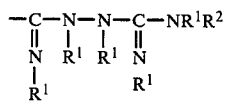
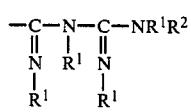
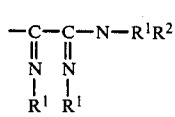
-continued
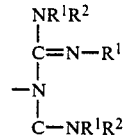
wherein R¹ and R² are as previously defined.
Examples
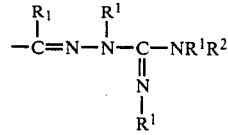
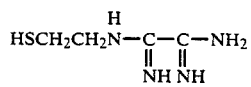
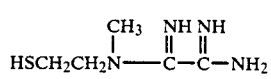
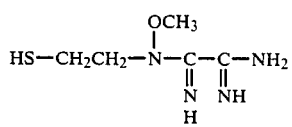
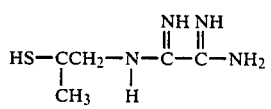
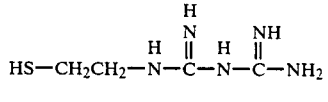
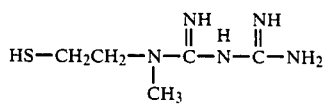
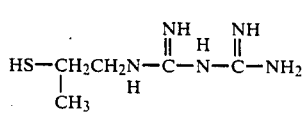

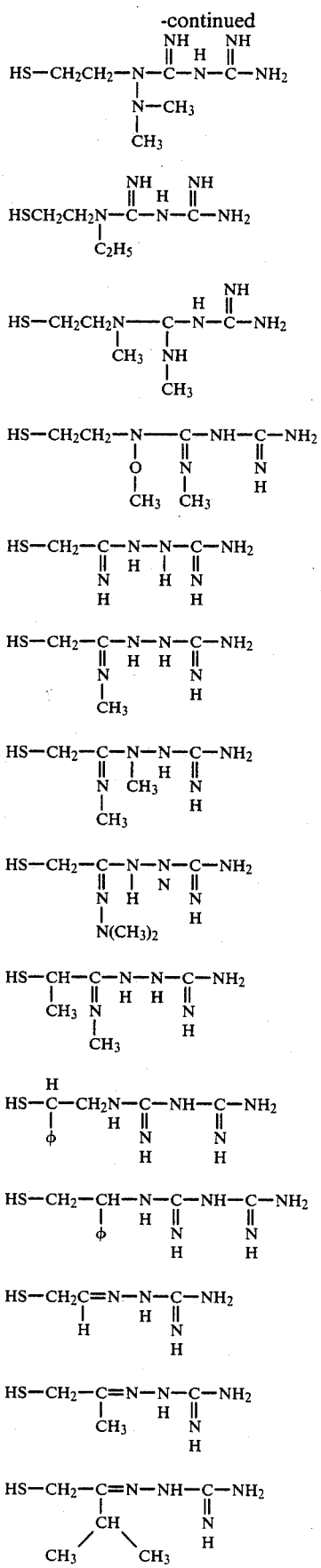

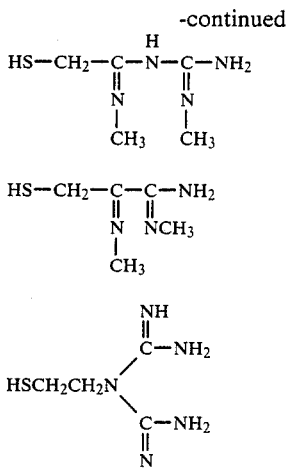

Identification of the Radical —COX'R³'

In the generic representation of the compounds of the present invention (I, above), the radical represented by —COX'R³' is, inter alia, —COOH (X' is oxygen and R³' is hydrogen) and all radicals known to be effective as pharmaceutically acceptable ester, anhydride (R³' is acyl) and amide radicals in the bicyclic β-lactam antibiotic art, such as the cephalosporins and penicillins and the nuclear analogues thereof.

Suitable radicals (R³' include conventional protecting or carboxyl blocking groups. The term "blocking group" as utilized herein is employed in the same manner and in accordance with the teaching of U.S. Pat. No. 3,697,515 which is incorported herein by reference. Pharmaceutically acceptable derivatives of the present invention falling in this class are given below. Suitable blocking esters thus include those selected from the following list which is representative and not intended to be an exhaustive list of possible ester groups, wherein X'=O and R³' is given:

(i) R³'=CR$^a$R$^b$R$^c$ wherein at least one of R$^a$, R$^b$ and R$^c$ is an electron-donor, e.g., p-methoxyphenyl. The remaining R$^a$, R$^b$ and R$^c$ groups may be hydrogen or organic substituting groups. Suitable ester groups of this type include p-methoxybenzyloyxcarbonyl.

(ii) R³'=CR$^a$R$^b$R$^c$ wherein at least one of R$^a$, R$^b$ and R$^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) R³'=CR$^a$R$^b$R$^c$ wherein at least two of R$^a$, R$^b$ and R$^c$ are hydrocarbon such as alkyl, e.g., methyl or ethyl, or aryl, e.g., phenyl and the remaining R$^a$, R$^b$ and R$^c$ group, if there is one, is hydrogen. Suitable esters of this type include t-butyloxycarbonyl, diphenylmethoxycarbonyl and triphenylmethoxycarbonyl.

Silyl esters, under this category of blocking groups, may conveniently be prepared from a halosilane of the formula:

$$R^4{}_3SiX'$$

wherein X' is a halogen such as chloro or bromo and R⁴ is alkyl, e.g., methyl, ethyl, t-butyl.

More generally stated, pharmaceutically acceptable carboxyl derivatives of the present invention are those derived by reacting I with alcohols, acylating reagents and the like. For example, esters and amides of interest are the above-listed starting materials and final products having the —COX'R³' group at the 2-position; wherein X' is oxygen, sulfur or NR' (R' is H or R³'), and R³' is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkylportion has 1-6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1-4 carbon atoms such as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the

group. Representative of such amides are those wherein R' is selected from the group consisting of hydrogen and lower alkyl such as methyl and ethyl.

The most preferred —COX'R³' radicals of the present invention are those wherein (relative to Structure I above), X is oxygen and R is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The following Examples illustrate but do not limit the process of the present invention. All temperatures are in °C.

EXAMPLE 1

Preparation of 4-(2-Acetoxyethyl)-azetidin-2-one

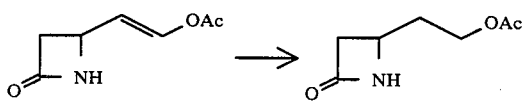

A mixture of 4-(2-acetoxyvinyl)-azetidin-2-one (3.00 g), 10% Pd/C (0.15 g) and ethylacetate(EtOAc) (120 ml) is hydrogenated in a 500 ml glass bomb on a Parr shaker at an initial pressure of 39 psi. After shaking 10 mins (final pressure of 20 psi), the mixture is filtered through a pad of MgSO₄ to remove the catalyst. The filtrate is concentrated in vacuo and the residue stripped with anhydrous benzene to provide 4-(2-acetoxyethyl)-azetidin-2-one (3.098 g) as a clear oil: ir(neat) 3.01, 5.66, 5.75, 7.28, 8.05, and 9.61 cm⁻¹; nmr(CDCl₃)δ 1.95 (m, 2), 2.07 (s, 3), 2.60 (m, 1), 3.12 (m, 1), 3.70 (m, 1), 4.15 (m, 2), and 6.77 (br s, 1).

EXAMPLE 2

Preparation of N-(t-Butyldimethylsilyl)-4-(2-acetoxyethyl)-azetidin-2-one

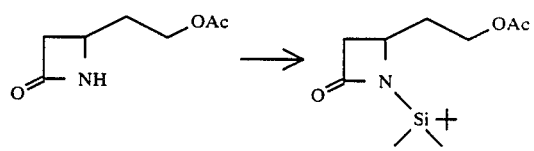

Triethylamine (Et₃N) (2.96 ml, 21.2 mmol) and t-butyldimethylsilyl chloride (3.059 g, 20.3 mmol) are added to an ice-cold stirring solution of 4-(2-acetoxyethyl)-azetidin-2-one (3.098 g, 19.3 mmol) in anhydrous dimethylformamide(DMF) (20 ml). A white precipitate appears immediately. The cooling bath is removed and the mixture is stirred at 25° C. (room temperature) for 5 mins. The mixture is diluted with benzene (200 ml), washed with H₂O (5×80 ml) and brine, dired with MgSO₄, filtered, and evaporated under reduced pressure to afford N-(t-butyldimethylsilyl)-4-(2-acetoxyethyl)-azetidin-2-one (5.078 g) as an off white solid; ir(neat) 5.75, 8.08, 8.41, 11.92, and 12.18 cm⁻¹; nmr (CDCl₃) δ 0.25 (s, 6), 0.98 (s, 9), 1.97 (m, 2), 2.05 (s, 3), 2.67 (dd, 1), 3.20 (dd, 1) 3.62 (m, 1), and 4.12 (t, 2); mass spectrum m/e 214 (M⁺-57) and 172.

EXAMPLE 3

Preparation of N-(t-Butyldimethylsilyl)-4-(2-hydroxyethyl)-azetidin-2-one

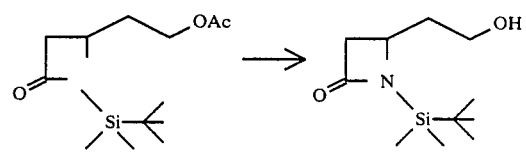

A solution of N-(t-butyldimethylsilyl)-4-(2-acetoxyethyl)-azetidin-2-one (41.7 g, 0.154 mol) in anhydrous methanol (415 ml) is stirred under a N₂ atmosphere with ice-bath cooling. A solution of sodium methoxide (415 mg, 7.7 mmol) in anhydrous methanol (15 ml) is added and the resulting solution is stirred in the cold for 2 more hrs. Acetic acid (2.2 ml) is then added and the solvents are evaporated in vacuo (i.v.). The residue is taken up in EtOAc (300 ml), washed with H₂O (4×75 ml), 5% NaHCO₃ (75 ml) and brine, dried with MgSO₄ and evaporated i.v. to a clear oil (21.3 g). This material is purified by chromatography on a Baker silica gel column (425 g, packed under EtOAc). After a 100 ml forefraction, 25 ml EtOAc fractions are collected every 2.5 mins. Fractions 41-49 yield starting material and fractions 51-90 afford N-(t-butyldimethylsilyl)-4-(2-hydroxyethyl)-azetidin-2-one (19.4 g) as a clear oil: ir (neat) 2.88, 5.73, 5.80, 7.52, 7.67, 7.99, 8.40, 11.95, and 12.18 cm⁻¹; nmr (CDCl₃) δ 0.25 (s, 6), 0.98 (s, 9), 1.82 (m, 2), 2.67 (dd, 1), 3.17 (dd, 1), 3.67 (t, 2), and 3.67 (m, 1); mass spectrum m/e 172.

EXAMPLE 4

Preparation of
N-(t-Butyldimethylsilyl)-4-(2-oxoethyl)-azetidin-2-one

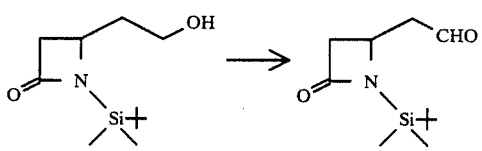

Anhydrous chromium trioxide (CrO₃) (1.94 g, 19.4 mmol) is added to a solution of anhydrous pyridine (3.07 g, 38.8 mmole) in anhydrous methylene chloride (CH₂Cl₂) (50 ml). The resulting mixture is stirred at room temperature for 15 mins. A solution of N-(t-butyl-dimethylsilyl)-4-(2-hydroxyethyl)-azetidin-2-one (0.74 g, 3.23 mmol) in anhydrous CH₂Cl₂ (5 ml) is added all at once. After stirring at room temperature for 5 mins, the mixture is decanted and the dark, gummy residue is washed with more CH₂Cl₂. The combined CH₂Cl₂ supernatant is evaporated i.v. The residue is tabken up in diethyl ether and filtered to remove chromium salts. The ethereal filtrate is washed with 5% NaHCO₃, 5% HCl, 5% NaHCO₃ and brine, dried with MgSO₄, filtered, and evaporated i.v. to yield N-(t-butyldimethyl-silyl)-4-(2-oxoethyl)-azetidin-2-one (0.54 g) as an off-white solid: ir(CHCl₃) 5.77, 5.80, 7.36, 7.60, 7.99, 8.50 and 11.95 cm⁻¹; nmr (CDCl₃) δ 0.23(s, 3), 0.27 (s, 3), 0.98 (s, 9), 2.63 (ddd, 1), 2.65 (dd, 1), 3.07 (ddd, 1), 3.37 (dd), 3.97 (m, 1), and 9.78 (t, 1); mass spectrum m/e 170 and 128.

EXAMPLE 5

Preparation of
N-(t-Butyldimethylsilyl)-4-(3-benzyloxycarbonyl-2-hydroxypropyl)-azetidin-2-one

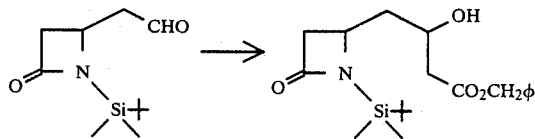

To a flame dried, 50 ml, 3-neck flask fitted with a N₂ inlet, magnetic stirrer, addition funnel, and serum cap are added anhydrous tetrahydrofuran (THF) (10.5 ml) and diisopropyl amine (0.579 ml, 4.13 mmol). The solution is cooled in an ice-methanol bath under N₂ and treated with 2.4N n-butyl lithium in hexane (1.72 ml). After being stirred at −10° for 15 mins, the solution is cooled to −78° and treated dropwise over 9 mins with a solution of benzyl acetate (0.620 g, 4.13 mmol) in anhydrous THF (3.5 ml). After stirring 15 more mins at −78° C., the reaction mixture is treated dropwise over 13 mins with a solution of N-(t-butyldimethylsilyl)-4-(2-oxoethyl)-azetidin-2-one (0.894 g, 3.93 mmol) in anhydrous THF (6 ml). The reaction mixture is stirred at −78° an additional 15 mins and then quenched with 2.5N HCl (6 ml). EtOAc (100 ml) is added and the organic phase is separated, washed with H₂O (2×20 ml), 5% NaHCO₃ (20 ml) and brine, dried with MgSO₄, and filtered. The filtrate is evaporated i.v. and the residue stripped with φH to yield N-(t-butyldimethylsilyl)-4-(3-benzyloxycarbonyl-2-hydroxypropyl)-azetidin-2-one (1.432 g) as an oil: ir (neat) 2.87, 5.73, 5.79, 7.57, 7.96, 8.39, 11.92, and 12.16 cm⁻¹; mass spectrum m/e 362, 320, 278, 170 and 128.

EXAMPLE 6

Preparation of
N-(t-Butyldimethylsilyl)-4-(3-benzyloxycarbonyl-2-oxopropyl)-azetidin-2-one

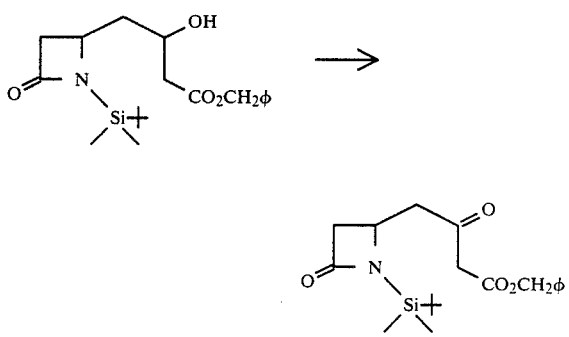

Anhydrous CrO₃ (2.274 g, 22.74 mmol) is added to a solution of anhydrous pyridine (3.597 g, 45.48 mmol) in anhydrous CH₂Cl₂ (60 ml). After stirring at room temperature (25° C.) for 15 mins, the reaction mixture is treated all at once with a solution of N-(t-butyldimethylsilyl)-4-(3-benzyloxycarbonyl-2-hydroxypropyl)-azetidin-2-one (1.432 g, 3.79 mmol) in anhydrous CH₂Cl₂ (25 ml). The resulting mixture is stirred at 25° C. for 5 mins. The CH₂Cl₂ layer is decanted from the dark, gummy residue which is triturated with more CH₂Cl₂. The combined CH₂Cl₂ phase is evaporated i.v. The residue is triturated with diethylether (Et₂O) (100 ml) in several portions and the Et₂O extracts are filtered to remove chromium salts. The ethereal filtrate is washed with 5% NaHCO₃, 1N HCl, 5% NaHCO₃ and brine, dried with MgSO₄, filtered, and evaporated i.v. to yield N-(t-butyldimethylsilyl)-4-(3-benzyloxycarbonyl-2-oxopropyl)-azetidin-2-one (1.042 g) as a pale yellow oil: ir (neat) 5.72 (3 poorly resolved peaks), 7.59 7.98, 8.42, and 11.93 cm⁻¹; nmr (CDCl₃) δ 0.18 (s, 3), 0.22 (s, 3), 0.97 (s, 9), 2.53 (dd, 1), 2.63 (dd, 1), 3.13 (dd, 1), 3.28 (dd, 1), 3.47 (s, 2), 3.88 (m, 1), 5.17 (s, 2), and 7.33 (s, 5); mass spectrum m/e 360, 318, and 2.76.

EXAMPLE 7

Preparation of
4-(3-Benzyloxycarbonyl-2-oxopropyl)-azetidin-2-one

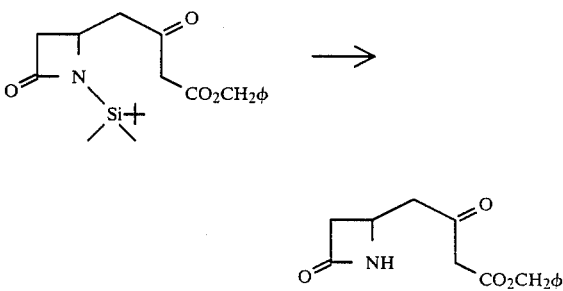

N-(t-butyldimethylsilyl)-4-(3-benzyloxycarbonyl-2-oxopropyl)-azetidin-2-one (302 mg, 0.80 mmol) is dissolved in acetic acid (4.0 ml) and the solution is diluted with H₂0(2.0 ml). The resulting solution is stirred in a securely stoppered, 10 ml, round-bottom flask in an oil bath maintained at 73° C. for 7 hrs. After cooling to room temperature, the reaction mixture is diluted with EtOAc and toluene and evaporated i.v. The residue is stripped twice with toluene to yield a yellow oil (220 mg). The crude product is chromatographed on Baker silica gel (8.8 g, packed under EtOAc). The column is eluted with EtOAc; 3 ml fractions being collected every 2.25 mins. Fractions 14–30 are combined and evaporated i.v. to provide 4-(3-benzyloxycarbonyl-2-oxopropyl)-azetidin-2-one (114 mg) as a clear oil: ir (neat) 3.04, 5.68, 5.72 and 5.83 cm⁻¹; nmr (CDCl₃) δ 2.52 (ddd, 1), 2.67 (dd, 1), 3.02 (dd, 1), 3.12 (ddd, 1), 3.48 (s, 2), 3.88 (m, 1), 5.18 (s, 2), 6.17 (m, 1), and 7.37 (s, 5); mass spectrum m/e 261 (M+), 233, 219, 192, 127 and 91.

EXAMPLE 8

Preparation of 4-(3-Benzyloxycarbonyl-3-diazo-2-oxopropyl)-azetidin-2-one

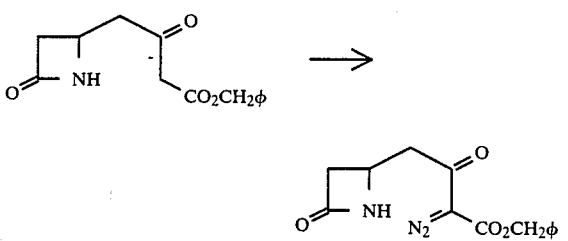

Freshly recrystallized p-carboxy benzene sulfonylazide (241 mg, 1.06 mmol) is added to a solution of 4-(3-benzyloxycarbonyl-2-oxopropyl)-azetidin-2-one (276 mg, 1.06 mmol) in anhydrous acetonitrile (6.6 ml). The resulting suspension is cooled in an ice-bath and stirred while Et₃N (443 μl, 3.18 mmol) is added. The resulting yellow solution is stirred at room temperature. A precipitate forms quickly. After 90 mins, the mixture is diluted with EtOAc (50 ml) and filtered. The filtrate is washed with H₂O (2×10 ml), 0.5N NaOH (2×10 ml), H₂O (4×10 ml) and brine, dried with MgSO₄, filtered, and evaporated i.v. to an off-white solid (273 mg). This is triturated with Et₂O to provide 4-(3-benzyloxycarbonyl-3-diazo-2-oxopropyl)-azetidin-2-one (227 mg) as a cream colored powder: ir (film from CHCl₃) 3.0, 4.65, 5.66, 5.82, 6.05, 7.21, 7.70 and 8.23 cm⁻¹; nmr (CDCl₃) δ 2.63 (ddd, 1), 2.97 (dd, 1), 3.15 (ddd, 1), 3.40(dd, 1), 3.98 (m, 1), 5.27 (s, 2), 6.13 (m, 1), and 7.38 (s, 5); mass spectrum m/e 259, 245, 231, and 218.

EXAMPLE 9

Preparation of Benzyl 1-azabicyclo[3.2.0]heptan-3,7-dione-2-carboxylate

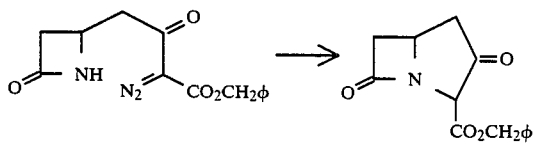

A solution of 4-(3-benzyloxycarbonyl-3-diazo-2-oxopropyl)-azetidin-2-one (20 mg) in anhydrous benzene (5 ml) is irradiated for 60 mins at room temperature using a Hanovia 450W medium-pressure mercury lamp and a Pyrex filter. Dry N₂ is bubbled through the solution prior to and during the photolysis. Evaporation of the solvent in vacuo gives an oil (17 mg) which is purified by chromatography on a 250μ×20×20 cm silica gel GF plate using 3:1 φH-EtOAc as developing solvent. The band at Rf 0.3 is removed and eluted with EtOAc to give a clear oil (2.4 mg). This material is further purified by tlc on a 250μ×7.5×8.5 cm silica gel GF plate. The cleanly resolved band at Rf 0.29 is removed and eluted with EtOAc to give benzyl 1-azabicyclo[3.2.0]heptan-3,7-dione-2-carboxylate (0.7 mg) as a clear oil: ir (CCl₄) 1783, 1773, and 1744 cm⁻¹; ir (CHCl₃) 1767, 1741 cm⁻¹; uv (Cy) 215 nm; nmr (CDCl₃) δ 2.36 (dd, J=8 and 18.5, 1), 2.90 (dd, J=6 and 18.5, 1), 2.92 (dd, J=2 and 16, 1), 3.63(dd, J=5 and 16, 1), 4.11 (m, 1), 4.71 (s, 1), 5.19 (s, 2) and 7.33 (s, 5); mass spectrum m/e 259 (M+), 231 (M+-28), 217 (M+-42), 203, 187, 186, 168 (M+-91), 124, and 91; high resolution mass spectrum m/e 259.0842 (C₁₄H₁₃NO₄).

EXAMPLE 10

Preparation of Benzyl 3-chloro-1-azabicyclo[3.2.0]hept-2-en-7-one-2-carboxylate

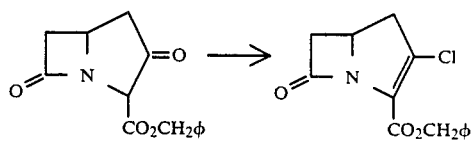

Benzyl 1-azabicyclo[3.2.0]heptane-3,7-dione-2-carboxylate (26 mg, 0.1 mmol) in anhydrous DMF (0.5 ml) containing PCl₃ (27 mg/0.2 mmol) is kept at 25° C. for 5 hours. The mixture is diluted with toluene (5 ml), washed with H₂O (5×1 ml), 5% HCl (2 ml), 5% NaHCO₃ (2 ml) and brine, dried with MgSO₄, and filtered. Evaporation of the solvent in vacuo provides crude benzyl 3-chloro-1-azabicyclo[3.2.0]hept-2-en-7-one-2-carboxylate.

EXAMPLE 11

Preparation of Benzyl 3-toluenesulfonyloxy-1-azabicyclo[3.2.0]hept-2-en-7-one-2-carboxylate

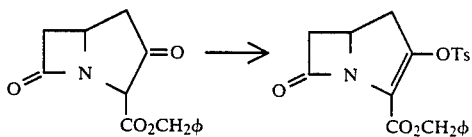

p-Toluenesulfonic anhydride (33 mg, 0.1 mmol) and Et₃N (17 μl, 0.12 mmol) are added to a solution of benzyl 1-azabicyclo[3.2.0]heptan-3,7-dione-2-carboxylate (26 mg., 0.1 mmol) in anhydrous CH₂Cl₂ (2 ml). The resulting solution is stirred at room temperature for 2 hours. The mixture is diluted with CH₂Cl₂ (10 ml), washed with H₂O (2×5 ml), pH 3 phosphate buffer (5 ml) and 5% NaHCO₃ (5 ml), dried with MgSO₄, filtered and evaporated i.v. to provide benzyl 3-toluenesulfonyloxy-1-azabicyclo[3.2.0]hept-2-en-7-one-2-carboxylate.

EXAMPLE 12

Preparation of Benzyl 6-(2,2,2-trifluoro-1-hydroxyethyl)-3-toluenesulfonyloxy-1-azabicyclo[3.2.0]hept-2-en-7-one-2-carboxylate

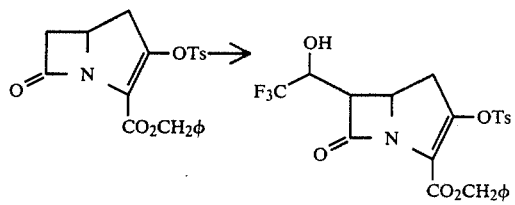

A solution of benzyl 3-toluenesulfonyloxy-1-azabicyclo[3.2.0]hept-2-en-7-one-2-carboxylate (41 mg) in anhydrous THF (0.5 ml) is added dropwise over 5 mins to a stirring solution of lithium diisopropylamide (from 15.5 μl of diisopropylamine and 70 μl of 1.6N BuLi) in anhydrous THF (1.5 ml) at −78°. The resulting solution is stirred under a $N_2$ atm at −78° for 10 mins and then trifluoroacetaldehyde (50 mg) is added all at once. After 1 more min, saturated aqueous NH4Cl solution (1.5 ml) is added and the mixture is allowed to warm to room temperature. The mixture is diluted with EtOAc (20 ml), washed with water and brine, dried with MgSO4, filtered, and evaporated in vacuo. The benzyl 6-(2,2,2-trifluoro-1-hydroxyethyl)-3-toluenesulfonyloxy-1-azabicyclo[3.2.0]hept-2-en-7-one-2-carboxylate.

EXAMPLE 13

Preparation of Benzyl 6-(3-phenyl-1-hydroxypropyl)-3-toluenesulfonyloxy-1-azabicyclo[3.2.0) hept-2-en-7-oxo-2-carboxylate

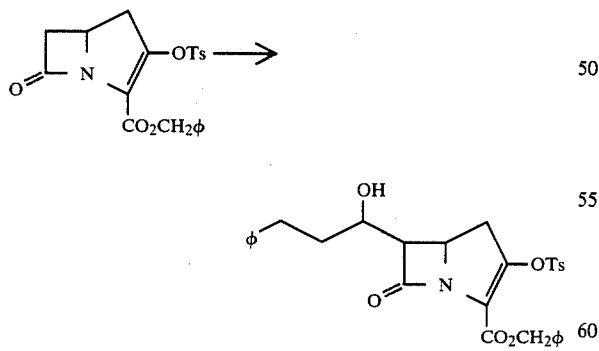

The procedure of Example 12 is duplicated except that 3-phenylpropionaldehyde (67 mg) is substituted for trifluoroacetaldehyde to provide benzyl 6-(3-phenyl-1-hydroxypropyl)-3-toluenesulfonyloxy-1-azabicyclo[3.2.0]hept-2-en-7-one-2-carboxylate.

EXAMPLE 14

Preparation of Benzyl 6-methyl-3-chloro-1-azabicyclo[3.2.0]hept-2-7-one-2-carboxylate

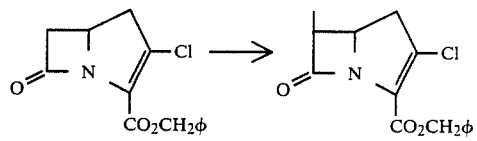

A solution of benzyl 3-chloro-1-azabicyclo[3.2.0]hept-2-en-7-one-2-carboxylate (56 mg) in anhydrous THF (0.5 ml) is added dropwise over a few minutes to a stirring solution of lithium diisopropylamide (from 31 μl diisopropylamine and 140 μl 1.6N BuLi) in anhydrous THF (3 ml) at −78°. After 15 more mins at −78°, the solution is treated with methyliodide (125 μl) and then allowed to warm to −20° over a period of 30 mins. Saturated aqueous NH4Cl (3 ml) is added and the mixture is allowed to come to room temperature. The mixture is diluted with EtOAc (50 ml), washed with pH 3 phosphate buffer, water, 5% NaHCO3, and brine, dried with magnesium sulfate, and evaporated in vacuo to give benzyl 6-methyl-3-chloro-1-azabicyclo[3.2.0]hept-2-en-7one-2-carboxylate.

EXAMPLE 15

Preparation of Benzyl 6-(1-hydroxyethyl)-6-methyl-3-chloro-1-azabicyclo[3.2.0]hept-2-en-7-one-2-carboxylate

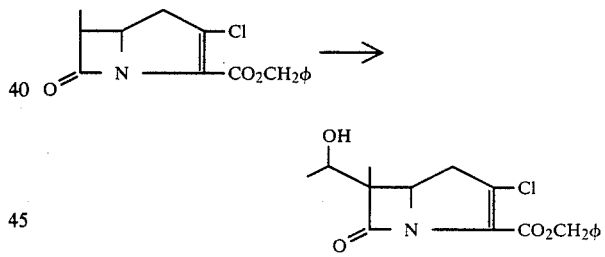

Benzyl 6-methyl-3-chloro-1-azabicyclo[3.2.0]hept-2-en-7-one-2-carboxylate is converted to its enolate derivative with lithium diisopropylamide in anhydrous THF at −78° as described in the previous example. To this solution is added 10 equivalents of acetaldehyde. Workup as described in example 12 yields benzyl 6-(1-hydroxyethyl)-6-methyl-3-chloro-1-azabicyclo[3.2.0]hept-2-en-7-one-2-carboxylate.

EXAMPLE 16

Preparation of Benzyl 6-(1-hydroxyethyl)-6-methyl-3-isopropylthio-1-azabicyclo[3.2.0]hept-2-en-t-one-2-carboxylate

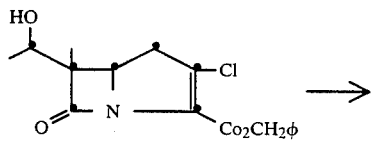

-continued

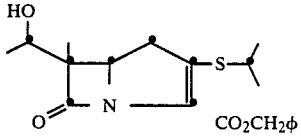

A solution of isopropylmercaptan (8 mg) in anhydrous dimethylformamide (DMF, 1 ml) containing 57% sodium hydride (4.4 mg) is added dropwise over 10 mins. to a stirring solution of benzyl 6-(1-hydroxyethyl-6-methyl-3-chloro-1-azabicyclo[3.2.0]hept-2-en-7-one-2-carboxylate (34 mg) in anhydrous DMF (2 ml) at −40° C. The resulting solution is stirred for 2 hours, with gradual warming to 0° C. The solution is diluted with ethyl acetate (20 ml), washed with water (5×10 ml) and brine, dried with MgSO₄, filtered, and evaporated in vacuo. The residue is purified by chromatography on silica gel to give benzyl 6-(1-hydroxyethyl)-6-methyl-3-isopropylthio-1-azabicyclo[3.2.0]hept-2-en-7-one-2-carboxylate.

EXAMPLE 17

Preparation of Sodium 6-(1-hydroxyethyl)-6-methyl-3-isopropylthio-1-azabicyclo[3.2.0]hept-2-en-7-one-2-carboxylate

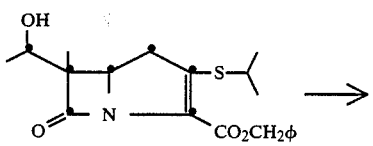

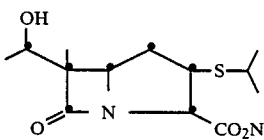

Benzyl 6-(1-hydroxyethyl)-6-methyl-3-isopropylthio-1-azabicyclo[3.2.0]hept-2-en-7-one-2-carboxylate (25 mg) is dissolved in dioxane (2 ml) and the solution is treated with water (1 ml) containing sodium bicarbonate (6 mg) and 10% palladium on powdered charcoal (25 mg). The resulting mixture is hydrogenated at 40 psi for 1 hour. The catalyst is filtered off and washed with water (3 ml). The combined filtrate is extracted with ethylacetate (3×2 ml), concentrated in vacuo, and lyophilized to afford sodium 6-(1-hydroxyethyl)-6-methyl-3-isopropylthio-1-azabicyclo[3.2.0]hept-2-en-7-one-2-carboxylate.

EXAMPLE 18

Preparation of Benzyl 6-(2,2,2-trifluoro-1-hydroxyethyl)-3-(2-dimethylaminoethylthio)-1-azabicyclo[3.2.0]hept-2-en-7-one-2-carboxylate

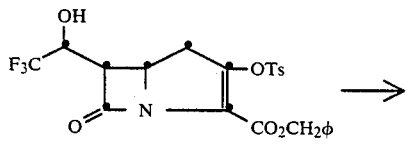

-continued

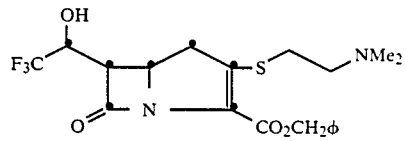

A mixture of benzyl 6-(2,2,2-trifluoro-1-hydroxyethyl)-3-toluenesulfonyloxy-1-azabicyclo[3.2.0]hept-2-en-7-one-2-carboxylate (51 mg), 2-(N,N-dimethylamino)ethylmercaptan hydrochloride (14.2 mg), and triethylamine (14 ml) in anhydrous DMF (2 ml) is stirred at room temperature for 2 hours. The mixture is diluted with ethyl acetate (20 ml), washed with 5% sodium bicarbonate (2×5 ml), water (4×10 ml), and brine, dried with MgSO₄, filtered, and concentrated in vacuo. The residue is purified by chromatography on silica gel to yield benzyl 6-(2,2,2-trifluoro-1-hydroxyethyl)-3-(2-dimethylaminoethylthio)-1-azabicyclo[3.2.0]hept-2-en-7-one-2-carboxylate.

EXAMPLE 19

Preparation of 6-(2,2,2-Trifluoro-1-hydroxyethyl)-3-(2-dimethylaminoethylthio)-1-azabicyclo[3.2.0]hept-2-en-7-one-2-carboxylic acid

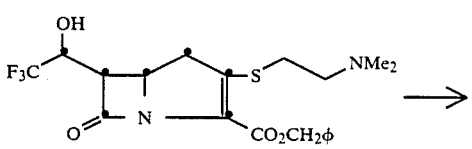

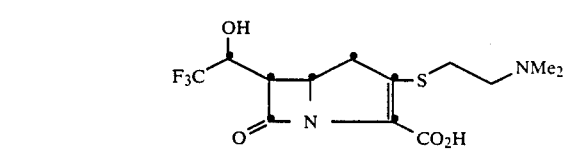

A mixture of benzyl 6-(2,2,2-trifluoro-1-hydroxyethyl)-3-(2-dimethylaminoethylthio)-1-azabicyclo[3.2.0]hept-2-en-7-one-2-carboxylate (30 mg), 10% palladium on powdered charcoal (30 mg), dioxane (3 ml), water (1.5 ml), and ethanol (0.5 ml) is hydrogenated at 45 psi for 1 hour. The catalyst is filtered off and washed with water (4 ml) and 0.1M pH 7 phosphate buffer (1 ml). The combined filtrate is washed with ethyl acetate (3×2 ml), concentrated in vacuo to ca. 1 ml, and charged onto a Dowex 50-X4 column (Na form). The product is eluted with DI water. The appropriate fractions are combined, concentrated in vacuo to ca. 5 ml., and lyophilized to give 6-(2,2,2-trifluoro-1-hydroxyethyl)-3-(2-dimethylaminoethylthio)-1-azabicyclo[3.2.0]hept-2-en-7-one-2-carboxylic acid.

EXAMPLE 20

Preparation of Benzyl 6-(3-phenyl-1-hydroxypropyl)-3-phenylthio-1-azabicyclo[3.2.0]hept-2-en-7-one-2-carboxylate

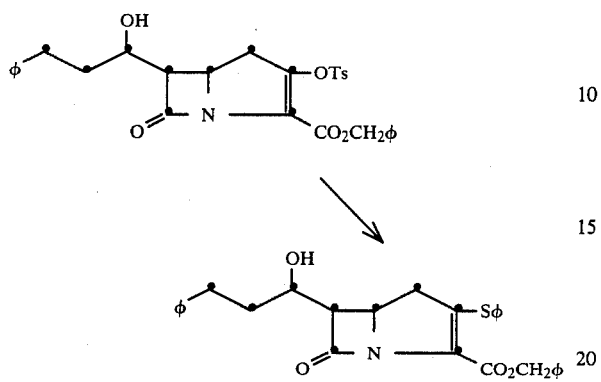

Thiophenol (11 mg) and N-isopropyl-N,N-diethylamine (13 mg) are added to an ice-cold, stirring solution of benzyl 6-(3-phenyl-1-hydroxypropyl)-3-touluensulfonyloxy-1-azabicyclo[3.2.0]hept-2-en-7-one-2-carboxylate (55 mg) in anhydrous DMF (2 ml). The resulting mixture is stirred in the cold for 15 mins and at room temperature for 2 hours. The mixture is diluted with ethylacetate (20 ml), washed with water (5×10 ml) and brine, dried with MgSO₄, filtered, and evaporated in vacuo. The residue is purified by silica gel chromatography to provide benzyl 6-(3-phenyl-1-hydroxypropyl)-3-phenylthio-1-azabicyclo[3.2.0]hept-2-en-7-one-2-carboxylate.

EXAMPLE 21

Preparation of Sodium 6-(3-phenyl-1-hydroxypropyl)-3-phenylthio-1-azabicyclo[3.2.0]hept-2-en-7one-2-carboxylate

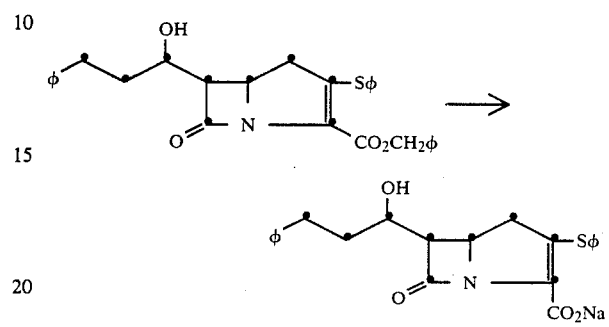

Benzyl 6-(3-phenyl-hydroxypropyl)-3-phenylthio-1-azabicyclo[3.2.0]hept-2-en-7-one-2-carboxylate is deblocked by the method of Example 17 to provide the title compound.

EXAMPLE 22

Following the procedure of the foregoing text and examples, the following compounds (I) are obtained by analogy

| Compound | $R^6$ | $R^7$ | $R^8$ | R | $R^9$ | Remarks |
|---|---|---|---|---|---|---|
| 1 | CH₃CH(OH)— | —CH₃ | —CH₂CH₂CH₃ | Na | | |
| 2 | CH₃CH(OH)— | —CH₃ | —CH₂CH₂NMe₂ | H | | Me = —CH₃ |
| 3 | CH₃CH(OH)— | —CH₃ | —C(CH₃)₂CH₂NH₂ | H | | |
| 4 | CH₃CH(OH)— | —CH₃ | —CH₂CH₂NH₂ | H | | |
| 5 | CH₃CH(OH)— | —CH₃ | —CH₂CH₂CH₂NH₂ | H | | |
| 6 | CH₃CH(OH)— | —CH₃ | phenyl | Na | | |
| 7 | CH₃CH(OH)— | —CH₃ | 4-NMe₂-phenyl | H | | |

-continued $$\begin{array}{c} R^6-\overset{R^7}{\underset{\|}{C}}-\overset{}{\underset{N}{\boxed{\phantom{xx}}}}-SR^8 \\ O \qquad\qquad COOR \end{array} \qquad I$$

| Compound | R⁶ | R⁷ | R⁸ | R | R⁹ Remarks |
|---|---|---|---|---|---|
| 8 | CH₃CH(OH)— | —CH₃ | 4-pyridyl | Na | |
| 9 | CH₃CH(OH)— | —CH₃ | 5-methyl-1,3,4-thiadiazol-2-yl | Na | |
| 10 | CH₃CH(OH)— | —CH₃ | 1-methyltetrazol-5-yl | Na | |
| 11 | CF₃CH(OH)— | H | —CH₂CH₂CH₃ | Na | |
| 12 | CF₃CH(OH)— | H | —CH₂CH₂NMe₂ | H | |
| 13 | CF₃CH(OH)— | H | —C(CH₂)₂CH₂NH₂ | H | |
| 14 | CF₃CH(OH)— | H | —CH₂CH₂NH₂ | H | |
| 15 | CF₃CH(OH)— | H | —CH₂CH₂CH₂NH₂ | H | |
| 16 | CF₃CH(OH)— | H | phenyl | Na | |
| 17 | CF₃CH(OH)— | H | 4-(NMe₂)phenyl | H | |
| 18 | CF₃CH(OH)— | H | 4-pyridyl | Na | |
| 19 | CF₃CH(OH)— | H | 5-methyl-1,3,4-thiadiazol-2-yl | Na | |
| 20 | CF₃CH(OH)— | H | 1-methyltetrazol-5-yl | Na | |
| 21 | φCH₂CH₂CH(OH)— | H | —CH₂CH₂CH₃ | Na | φ = phenyl |

-continued

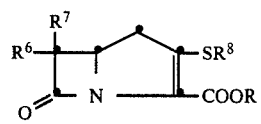  I

| Compound | R⁶ | R⁷ | R⁸ | R | R⁹ Remarks |
|---|---|---|---|---|---|
| 22 | φCH₂CH₂CH(OH) | H | —CH₂CH₂NMe₂ | H | |
| 23 | φCH₂CH₂CH(OH) | H | —C(CH₃)₂CH₂NH₂ | H | |
| 24 | φCHCHCH(OH) | H | —CH₂CH₂NH₂ | H | |
| 25 | φCH₂CH₂CH(OH) | H | —CH₂CH₂CH₂NH₂ | H | |
| 26 | φCH₂CH₂CH(OH) | H | phenyl | Na | |
| 27 | φCH₂CH₂CH(OH) | H | 4-NMe₂-phenyl | H | |
| 28 | φCH₂CH₂CH(OH) | H | 4-pyridyl | Na | |
| 29 | φCH₂CH₂CH(OH) | H | 2-methyl-1,3,4-thiadiazol-5-yl | Na | |
| 30 | φCH₂CH₂CH(OH) | H | 1-methyl-1H-tetrazol-5-yl | Na | |
| 31 | H | H | CH₂CH₂CH₃ | Na | |
| 32 | H | H | CH₂CH₂NMe₂ | H | |
| 33 | H | H | C(CH₃)₂CH₂NH₂ | H | |
| 34 | H | H | CH₂CH₂NH₂ | H | |
| 35 | H | H | CH₂CH₂CH₂NH₂ | H | |
| 36 | H | H | phenyl | Na | |
| 37 | H | H | 4-NMe₂-phenyl | H | |
| 38 | H | H | 4-pyridyl | Na | |

-continued

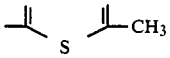

| Compound | R[6] | R[7] | R[8] | R | R[9] | Remarks |
|---|---|---|---|---|---|---|
| 39 | H | H | ![N-N with S, CH3] | | Na | |
| 40 | H | H | ![N-N with N-CH3] | | Na | |

EXAMPLE 23

Benzyl 1-azabicyclo[3.2.0]heptan-3,7-dione-2-carboxylate

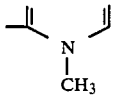

A mixture of 4-(3-benzyloxycarbonyl-3-diazo-2-oxopropyl)-azetidin-2-one (718 mg, 2.5 mMol), rhodium (II) acetate (5 mg) and anhydrous benzene (50 ml) is deoxygenated by bubbling nitrogen through it for 45 minutes. The mixture is then stirred and heated in an oil bath maintained at 80° C. for 70 minutes. After cooling to room temperature, the mixture is filtered and the filtrate is evaporated under vacuum to an oil. Crystallization from ethyl acetate (5 ml)-diethylether (20 ml) provides benzyl 1-azabicyclo[3.2.0]heptan-3,7-dione-2-carboxylate (502 mg, 77% yield) as small, white prisms: mp 100°–102°; IR ($CH_2Cl_2$) 1770; 1741 $cm^{-1}$; UV (dioxane) 220 nm; NMR ($CDCl_3$, 300 MHz) δ 2.43 (dd, 1, J=8 and 19, H4a), 2.94 (dd, 1, J=6.5 and 19, H4b), 2.99 (dd, 1, J=2 and 16, H6B), 3.63 (dd, 1, J=5 and 16, H6α), 4.18 (m, 1, H5), 4.76 (S, 1, H2), 5.23 (S, 2, $CH_2\phi$), and 7.40 (S, 5, ArH); MS m/e 259 (M+), 231 (M+-28), 217 (M+-42), 203, 187, 186, 168 (M+-91), 124, and 91.

Anal. Calculated for $C_{14}H_{13}NO_4$: C, 64.86; H, 5.05; N, 5.40. Found: C, 64.92; H, 5.01; N, 5.11.

EXAMPLE 24

Dicyclohexylammonium 1-azabicyclo[3.2.0]heptan-3,7-dione-2-carboxylate

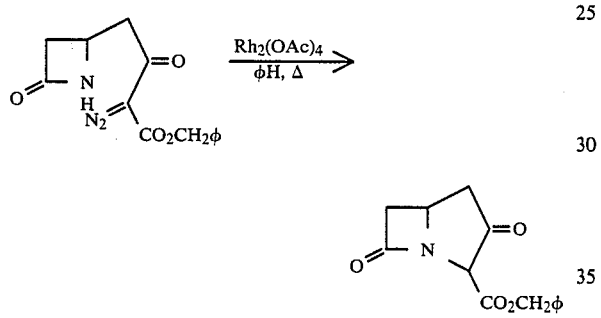

A solution of benzyl 1-azabicyclo[3.2.0]heptan-3,7-dione-2-carboxylate (25.9 mg, 0.1 mMol) in dioxane (1.5 ml) is added to a mixture of 10% palladium on charcoal (5 mg) and dioxane (1.0 ml) which had been equilibrated under an atmosphere of hydrogen for 10 minutes. The resulting mixture is stirred under 1 atmosphere of hydrogen at room temperature for 30 mins., during which time 2.6 ml of hydrogen are absorbed. The mixture is filtered and the catalyst is washed with more dioxane (0.5 ml). The filtrate, which contains 1-azabicyclo[3.2.0]heptan-3,7-dione-2-carboxylic acid, is divided into two equal 1.5 ml portions.

One portion of the dioxane filtrate is treated with a solution of dicyclohexylamine (9.1 mg, 0.05 mMol) in dioxane. The solvent is removed under vacuum and the residue is triturated with diethyl ether to yield dicyclohexylammonium 1-azabicyclo[3.2.0]heptan-3,7-dione-2-carboxylate as a white powder: IR (Nujol) 1764, 1637 $cm^{-1}$; NMR ($D_2O$) δ 1.1–2.2 (m, —$CH_2CH_2CH_2CH_2CH_2$—), 2.64 (dd, J=7.8 and 19.0, H4a), 2.89 (dd, J=7.9 and 19.0, H4b), 3.08 (dd, J=2 and 16.6 H6β), 3.26 (m, N—CH), 3.61 (dd, J=4.7 and 16.6, H6α), 4.17 (m, H5), and 4.8 (br s, HOD, obscures H2 resonance).

EXAMPLE 25

Benzyl 3-(p-toluenesulfonyloxy)-1-azabicyclo[3.2.0]hept-2-en-7-one-2-carboxylate

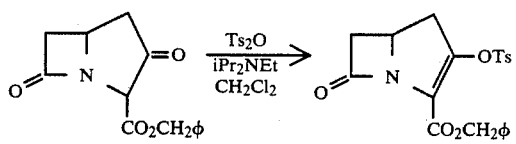

p-Toluenesulfonic anhydride (326 mg, 1 mμol) and N,N-diisopropylethylamine (192 μl, 1.1 mμol) are added to an ice-cold, stirring solution of benzyl 1-azabicyclo[3.2.0]heptan-3,7-dione-2-carboxylate (259 mg, 1 mμol) in anhydrous methylene chloride (10 ml). The resulting solution is stirred in the cold and under a nitrogen atmosphere for 2.5 hours. The solution is diluted with methylene chloride (20 ml), washed with water (10 ml), 1M pH3 phosphate buffer (10 ml) and 5% aqueous sodium bicarbonate (2×10 ml) dried with magnesium sulfate, filtered, and evaporated under vacuum to a semi-solid. This material is triturated with ice-cold ethyl acetate (2×2 ml) and diethyl ether (2×5 ml) to provide benzyl 3-(p-toluenesulfonyloxy)-1-azabicyclo[3.2.0]hept-2-en-7-one-2-carboxylate (276 mg, 67%) as a white powder. Recrystallization from methylene chloride-diethyl ether gives analytically pure product as small white needles: mp 103°–105°; IR ($CH_2Cl_2$) 1786, 1723, 1382, and 1190 cm$^{-1}$; NMR ($CDCl_3$) δ 2.44 (s, 3, $ArCH_3$) 3.03 (dd, 1, J=3.0 and 17.0, H6β), 3.16 (dd, 1, J=8.5 and 18.7, H4a), 3.32 (dd, 1, J=10.0 and 18.7, H4b), 3.55 (dd, 1, J=5.5 and 17.0, H6α), 4.21 (m, 1, H5), 5.14 (ABq, 2, J=12, $CH_2Ar$), 7.35 (S, 5, ArHN, 7.26 and 7.75 (two d's, 4, J=9, ArH); UV(dioxane) 283 (ε6600) and 277 (ε6500) nm.

Anal., Calculated for $C_{21}H_{19}NO_6S$: C, 61.01; H, 4.63; N, 3.39. Found: C, 59.94; H, 4.47; N, 3.26.

EXAMPLE 26

Benzyl 3-(p-nitrobenzenesulfonyloxy)-1-azabicyclo[3.2.0]hept-2-en-7-one-2-carboxylate

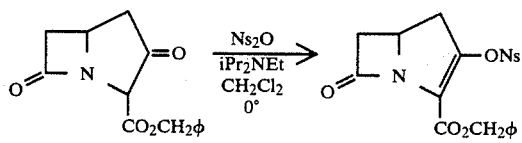

An ice-cold solution of benzyl 1-azabicyclo[3.2.0]heptan-3,7-dione-2-carboxylate (20 mg, 0.077 mmol) in methylene chloride (2 ml) is treated with p-nitrobenzenesulfonic anhydride (37.3 mg, 0.096 mmol) and N,N-diisopropylethylamine (18.3 μl, 0.015 mmol). After stirring in the cold for 20 minutes, the solution is diluted with cold methylene chloride (1 ml) and cold 0.1M pH 7 phosphate buffer (2 ml) and shaken. The organic phase is separated, washed with cold 0.1M pH7 phosphate buffer (2×2 ml), water and brine, dried with magnesium sulfate, and filtered. The filtrate is diluted with cold methanol (0.5 ml) and quickly evaporated under vacuum to give a solid. The crude product is triturated with cold methanol and dried under vacuum to provide benzyl 3-(p-nitrobenzenesulfonyloxy)-1-azabicyclo[3.2.0]hept-2-en-7-one-2-carboxylate (26 mg) as a white solid: mp 86°–88°; IR ($CH_2Cl_2$) 1794, 1723, 1521, and 1344 cm$^{-1}$; UV ($CHCl_3$) 257 (ε 10,600) and 280 (ε 7,600) nm; NMR ($CDCl_3$) δ 3.08 (dd, 1, J=3.6 and 17, H6β), 3.25 (dd, 1, J=8.8 and 18, H3a), 3.35 (dd, 1, J=9.8 and 18, H4b), 3.59 (dd, 1, J=5.4 and 17, H6α), 4.26(m, 1, H5), 5.10 (ABq, 2, J=21.2, $CH_2\phi$), 7.32 (s, 5, $C_6H_5$), 8.03 and 8.22 (two d's, 4, J=9.3, $NO_2C_6H_4$).

Preparation of p-nitrobenzene sulfonic anhydride

A mixture of p-nitrobenzensulfonic acid (20 g), phosphorous pentoxide (50 g) and 1,2-dichloroethylene (100 ml) is heated at reflux for 4 days. The hot supernatant is decanted from the gummy residue and allowed to cool to room temperature. The resulting crystalline precipitate of p-nitrobenzenesulfonic anhydride (1.5 g) is collected, washed with anhydrous diethylether, and dried under vacuum. The gummy residue is twice more refluxed overnight with 100 ml portions of dichloroethylene and worked up as above to provide additional p-nitrobenzenesulfonic anhydride (4.0 g); mp 171°–172°.

EXAMPLE 27

Benzyl 3-diphenylphosphoryl-1-azabicyclo[3.2.0]hept-2-en-7-one-2-carboxylate

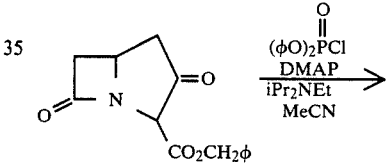

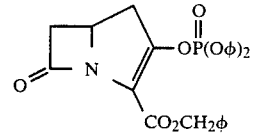

An ice-cold, stirring solution of benzyl 1-azabicyclo[3.2.0]heptan-3,7-dione-2-carboxylate (13 mg, 0.05 mMol), 4-dimethylamino pyridine (1.2 mg, 0.01 mMol) and N,N-diisopropylethylamine (12.2 μl, 0.07 mMol) in anhydrous acetonitrile (0.5 ml) is treated with diphenyl chlorophosphate (12.4 μl, 0.06 mMol). The resulting solution is stirred in the cold and under a nitrogen atmosphere for 2 hours, then diluted with methylene chloride (5 ml), washed with water (2 ml), 0.1M pH 7 phosphate buffer (2 ml) and brine, dried over magnesium sulfate, and filtered. Evaporation of the filtrate under vacuum leaves crude benzyl-3-diphenylphosphoryl-1-azabicyclo[3.2.0]-hept-2-en-7-one-2-carboxylate (22 mg) as an oil: UV (dioxane) 281 nm; NMR($CDCl_3$) δ 2.90 (dd, 1, J=3 and 17, H6β), 3.17(m, 2, H4a and H4b), 3.52 (dd, 1, J=5.5 and 17, H6α), 4.13(m, 1, H5), 5.28(S, 2, $CH_2\phi$), and 7.30(m, 15, ArH).

EXAMPLE 28

N-(t-Butyldimethylsilyl)-4-[3-(p-nitrobenzyloxycarbonyl)-2-hydroxypropyl]-azetidin-2-one

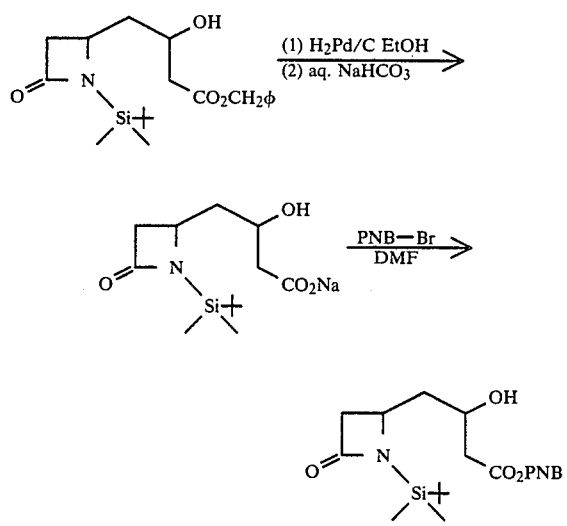

A mixture of crude N-(t-butyldimethylsilyl)-4-(3-benzyloxycarbonyl-2-hydroxypropyl]-azetidin-2-one (11.33 g, 30 mmol), ethanol (300 ml) and 10% palladium on charcoal (1.13 g) is hydrogenated at 50 psi for 1 hour. The mixture is filtered and the filtrate is treated with water (150 ml) containing sodium bicarbonate (2.52 g, 30 mmol) and concentrated under vacuum to ca 100 ml. The aqueous concentrate is washed with ethyl acetate (2×100 ml) and lyophilized to provide the sodium carboxylate (7.70 g) as a white powder.

The sodium salt and p-nitrobenzyl bromide (6.48 g, 30 mmol) are dissolved in anhydrous dimethyl formamide (150 ml) under a nitrogen atmosphere. After standing for 1 hour at room temperature, the solution is evaporated under vacuum to a semi-solid. The residue is taken up in ethyl acetate (200 ml), washed with water (2×200 ml) and brine, dried over magnesium sulfate, filtered, and evaporated under vacuum. The residual yellow oil is chromatographed on silica gel (250 g) using 1:1 toluene-ethyl acetate as eluting solvent to provide N-(t-butyldimethylsilyl)-4-[3-(p-nitrobenzyloxycarbonyl)-2-hydroxypropyl]-azetidin-2-one (8.92 g, 70%) as an oil which solidified on standing: IR (CH$_2$Cl$_2$) 3585, 1733, 1527, and 1350 cm$^{-1}$; NMR(CDCl$_3$) δ 0.22 (s, 3, CH$_3$), 0.25 (s, 3, CH$_3$), 0.93 (s, 9, C(CH$_3$)$_3$), 1.16–2.33 (m, 2, CH—CH$_2$—CH), 2.40–3.47 (m, 3, OH and H3α and H3β), 2.55 (d, 2, J=6, CH$_2$CO$_2$), 3.50–4.33 (m, 2, H4, and CH—OH), 5.30 (s, 2, CH$_2$Ar), and 7.55, 8.27 (two d's, 4, J=8.5, ArH).

EXAMPLE 29

N-(t-Butyldimethylsilyl)-4-[3-(p-nitrobenzyloxycarbonyl)-2-hydroxypropyl)-azetidin-2-one

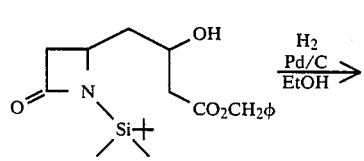

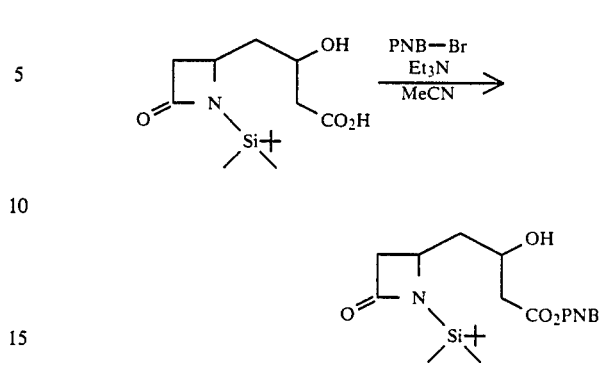

A mixture of crude N-(t-butyldimethylsilyl)-4-(3-benzyloxycarbonyl-2-Hydroxypropyl)-azetidin-2-one (13.46 g, 35.6 mmol), 10% palladium on charcoal, and ethanol (200 ml) is hydrogenated at 40 psi for 30 mins. The mixture is filtered and the filtrate is evaporated under vacuum and stripped with toluene to give N-(t-butyldimethylsilyl)-4-(3-carboxy-2-hydroxypropyl)-azetidin-2-one (9.51 g) as an off-white solid: IR (neat film from Me$_2$CO) 3200 (br), 1735, and 1700 (shifts to 1590 with Et$_3$N) cm$^{-1}$; NMR (Me$_2$CO-d$_6$) δ 0.25 (s, 6, 2CH$_3$), 0.98 (s, 9, C(CH$_3$)$_3$) 1.17–2.33 (m, 2, CH—CCH$_2$—CH), 2.50 (d, 2, J=6.5, CH$_2$CO$_2$), 2.50–3.40 (m, 2, H3 and H3β), 3.97 (m, 2, H4 and CHOH); MS on bistrimethylsilyl derivative m/e 431 (M+), 416(M+-57) and 332 (374-42).

The crude carboxylic acid is suspended in anhydrous acetonitrite (150 ml) and treated with p-nitrobenzyl bromide (7.56 g, 35 mμol) and triethylamine (4.9 ml, 35 mμol). The resulting solution is kept at room temperature for 2 days and then in a refrigerator for 3 days. The reddish orange solution is evaporated under vacuum and the residue shaken with ethyl acetate (100 ml, 2×50 ml) and filtered to remove triethylammonium bromide. The ethyl acetate filtrate is washed with water (3×100 ml) and brine, dried with magnesium sulfate, filtered, and evaporated under vacuum to an amber oil (13.62 g). Crystallization from diethyl ether affords N-(t-butyldimethylsilyl)-4-[3-(p-nitrobenzyloxycarbonyl)-2-hydroxypropyl]azetidin-2-one (6.84 g) as an off-white powder. Chromatography of the mother liquors on a silica gel column using 1:1 toluene-ethyl acetate as eluting solvent affords addition product (3.14 g) as an oil which solidifies.

EXAMPLE 30

N-(t-Butyldimethylsilyl)-4-[3-(p-nitrobenzyloxycarbonyl)-2-oxopropyl]-azetidin-2-one

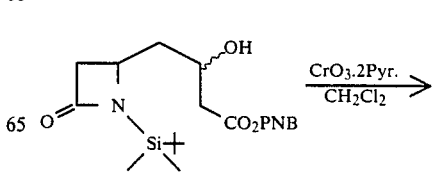

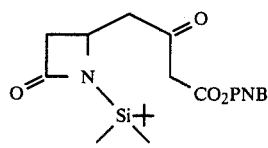

Anhydrous chromium trioxide (16.88 g 169 mmol) is added to a solution of anhydrous pyridine (27.3 ml, 338 mmol) in anhydrous methylene chloride (470 ml). The resulting mixture is stirred at room temperature for 30 minutes and then treated with a solution of N-(t-butyl-dimethylsilyl)-4-[3-(p-nitrobenzyloxycarbonyl)-2-hydroxypropyl]-azetidin-2-o one (8.92 g, 21.1 mmol) in methylene chloride (80 ml). The reaction mixture is stirred an additional 15 minutes at room temperature and then treated with 2-propanol (6.75 ml). The methylene chloride phase is decanted from the dark, tary residue and evaporated under vacuum. The residue from this operation is triturated with diethyl ether (350 ml) and filtered through a pad of magnesium sulfate which is washed with additional ether (150 ml). The ethereal filtrate is washed with water (200 ml), 5% aqueous sodium bicarbonate (200 ml) and brine, dried with magnesium sulfate, filtered, evaporated under vacuum, and stripped with toluene to afford the crude product (5.99 g) as an amber oil. Chromatigraphy on a silica gel column using 3:2 petroleum etherethyl acetate as eluting solvent yields N-(t-butyldimethylsilyl)-4-[3-(p-nitrobenzyloxycarbonyl)-2-oxopropyl]-azetidin-2-one (5.17 g, 58%) as a pale yellow, viscous oil which solidifies. Trituration with diethyl ether gives the product as small, white crystals: mp 65°–66.5°, IR (CH$_2$Cl$_2$) 1732, 1522, and 1350 cm$^{-1}$, NMR (CDCl$_3$) δ 0.20 (s, 3, CH$_3$), 0.23 (s, 3, CH$_3$), 0.93 (s, 9, C(CH$_3$)$_3$), 2.58 (dd, 1, J=2.7 and 15.7, H3β), 2.72 (dd, 1, J=9.4 and 18.2, CH$_2$COCH$_2$CO$_2$), 3.19 (dd, 1, J=4.0 and 18.2, CHCOCH$_2$CO$_2$), 3.35 (dd, 1, J=5.3 and 15.7, H3α), 3.55 (s, 2, COCH$_2$CO$_2$), 3.90 (m, 1, H4), 5.30 (s, 2, CH$_2$Ar), 7.55 and 8.25 (two d, 4, J=8.5, ArH); MS m/e 405 (M$^+$-15), 363 (M$^+$-57), 321 (363-42) and 136.

Anal, Calculated for C$_{20}$H$_{28}$N$_2$O$_6$Si: C, 57.12; H, 6.71; N, 6.66. Found: C, 57.28; H, 6.75; N, 6.60.

EXAMPLE 31

4-[3-(P-Nitrobenzyloxycarbonyl)-2oxopropyl]azetidin-2-one

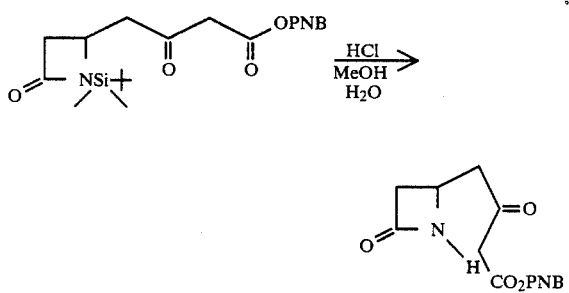

A solution of N-(t-butyldimethylsilyl)-4-[3-(p-nitrobenzyloxycarbonyl)-2-oxopropyl]-azetidin-2-one (5.17 g, 12.3 mMol) in methanol (55 ml) is treated with 1N hydrochloric acid (6.2 ml) and then kept at room temperature for 200 mins. The solution is treated with 1M dipotassium hydrogenphosphate (6.2 ml) and concentrated under vacuum. The residue is taken up in ethyl acetate (100 ml), washed with brine, dried over magnesium sulfate, filtered, and evaporated under vacuum. Triturating the resulting oil with diethyl ester yields 4-[3-(p-nitrobenzyloxycarbonyl)-2-oxopropyl]-azetidin-2-one (3.42 g, 91%) as an off-white powder: mp 50°–52°; IR (CH$_2$Cl$_2$) 3416, 1767, 1723, 1528, and 1352 cm$^{-1}$; NMR (CDCl$_3$) δ 2.60 (ddd, 1, J=1, 2.7, and 15.1, H3β), 2.77 (dd, 1, J=8.4 and 18.2, CHCH$_2$CO), 3.13 (dd, 1, J=5.1 and 18.2, CHCH$_2$CO), 3.20 (ddd, 1, J=2.4, 5.0, and 15.1, H3α), 3.57 (s, 2, COCH$_2$CO$_2$), 3.98 (m, 1, H4); 5.27 (s, 2, CH$_2$Ar), 6.28 br s, 1, NH), 7.53 and 8.23 (two d's, 4, J=8.5, ArH); mass spectrum m/e 306(M+), 264(M+-42), 237, 153, 125, 111, and 136.

EXAMPLE 32

4-[3-(P-Nitrobenzylorycarbonyl)-3-diazo-2-oxopropyl]azetidin-2-one

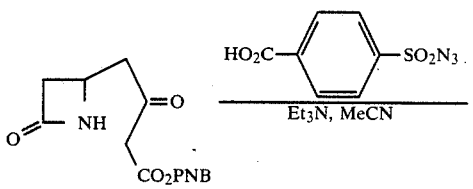

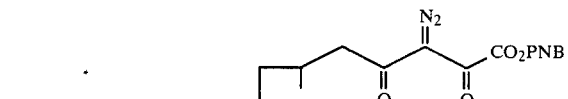

p-Carboxybenzyenesulfonylazide (2.67 g, 11.8 mMol) and triethylamine (4.68 ml, 33.6 mMol) are added to an ice-cold, stirring solution of 4-[3-(p-nitrobenzyloxycarbonyl)-2-oxopropyl]-azetidin-2-one (3.42 g, 11.2 mMol) in anhydrous acetonitrile (70 ml). The resulting mixture is stirred in the cold for 10 minutes and at room temperature for 60 minutes. The mixture is diluted with ethyl acetate (200 ml) and filtered. The filtrate is washed with water (2×100 ml), 1M pH3 phosphate buffer (50 ml), 0.1M pH7 phosphate buffer (100 ml), and brine, dried over magnesium sulfate, filtered, and evaporated under vacuum to a yellow foam (3.75 g). The crude product is taken up in methylene chloride (ca. 10 ml), heated briefly with activated charcoal, and filtered through a pad of magnesium sulfate. The filtrate is diluted with diethyl ether (ca. 40 ml) and scratched to yield a precipitate. The precipitate is collected, washed with ether, and dried under vacuum to provide 4-[3-(p-nitrobenzyloxycarbonyl)-3-diazo-2-oxopropyl]azetidin-2-one (3.29 g, 88%) as a pale yellow powder: mp 114.5°–116.5°; IR (CH$_2$Cl$_2$) 3413, 2142, 1767, 1724, 1657, 1530, and 1352 cm$^{-1}$; NMR (CDCl$_3$) δ 2.68 (ddd, 1, J=1.2, 2.7, and 14.8, H3β), 3.02 (dd, 1, J=8.4 and 18.0, CHCH$_2$CO), 3.22 (ddd, 1, J=2.4, 4.8, and 14.8, H3α); 343 (dd, 1, J=4.6 and 18.0, CHCH$_2$CO), 4.00 (m, 1, H4), 5.38 (s, 2, CH$_2$Ar), 6.30 (brs, 1, NH), 7.57 and 8.27 (two d's, 4, J=8.5, ArH); mass spectrum m/e 332(M+), 304(M+-28), 290(M+-42), 262, and 263.

Anal., calculated for C$_{14}$H$_{12}$N$_4$O$_6$: C, 50.61; H, 3.64; N, 16.86. Found: C, 50.34; H, 3.42; N, 16.72.

EXAMPLE 33

P-Nitrobenzyl 1-azabicyclo[3.2.0]heptan-3,7-dione-2-carboxylate

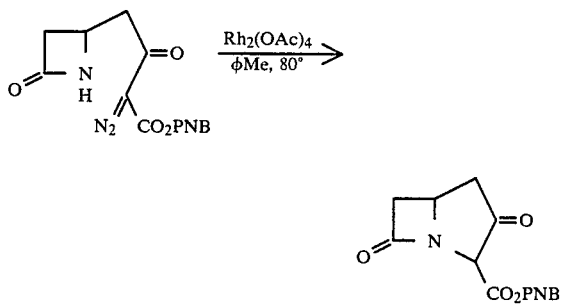

A suspension of 4-[3-(p-nitrobenzylocycarbonyl)-3-diazo-2-oxopropyl]-azetidin-2-one (2.93 g) and rhodium (II) acetate (15 mg) in anhydrous toluene (300 ml) is degassed by bubbling nitrogen through it for 60 minutes. The mixture is then stirred and heated in an oil bath maintained at 80° C. After a few minutes, the diazo compound dissolves and gas evolution commences. The mixture is heated at 80° C. for 100 minutes, then allowed to stand at room temperature for 30 mins. before filtering through a pad of celite. The filtrate is evaporated under vacuum to an oily residue which is triturated with diethyl ether to afford p-nitrobenzyl 1-azabicyclo[3.2.0]heptan-3,7-dione-2-carboxylate (2.53 g, 94%) as an off-white powder. Recrystallization from ether provides analytically pure product: mp 127°–128°: IR (CH$_2$Cl$_2$) 1776, 1753, 1529, and 1352 cm$^{-1}$; NMR (CDCl$_3$) δ 2.47 (dd, 1, J=8.2 and 18.8, H4a), 2.98 (dd, 1, J=6.8 and 18.8, H4b), 3.00 (dd, 1, J=2.0 and 12.0, H6β), 3.70 (dd, 1, J=4.8 and 12.0, H6α), 4.20 (m, 1, H5), 4.80 (s, 1, H2), 5.32 (s, 2, CH$_2$Ar), 7.57 and 8.25 (two d's, 4, J=8, ArH); mass spectrum m/e 304(M+), 276(M+-28), 262 (M+-42), and 168(M+-136).

Anal., calculated for C$_{14}$H$_{12}$N$_2$O$_6$: C, 55.27; H, 3.98; N, 9.21. Found: C, 55.06; H, 4.03; N, 8.99.

EXAMPLE 34

P-Nitrobenzyl 3-(p-Toluenesulfonyloxy)-1-azabicyclo[3.2.0]hept-2-en-7-one-2-carboxylate

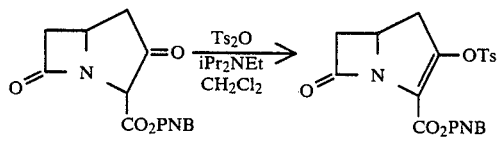

p-toluenesulfonic anhydride (520 mg, 1.59 mmol) and N,N-diisopropylethylamine (300 μl, 1.72 mmol) are added to an ice-cold, stirring solution of p-nitrobenzyl 1-azabicyclo[3.2.0]heptan-3,7-dione-2-carboxylate (484 mg, 1.59 mmol) in anhydrous methylene chloride (17 ml). The resulting solution is stirred in the cold for 2 hours, then diluted with more methylene chloride, washed with water, 1μ ph 3.4 phosphate buffer and saturated aqueous sodium bicarbonate, dried with magnesium sulfate, filtered, and evaporated under vacuum. Addition of cold ethyl acetate and a few seed crystals to the oily residue induces crystallization. The product is collected, washed with cold ethyl acetate, and dried under vacuum to afford p-nitrobenzyl 3-(p-toluenesulfonyloxy)-1-azabicyclo[3.2.0]hept-2-en-7-one-2-carboxylate (446 mg, 61%) as off-white crystals: mp 99°–102° (dec.); IR (neat) 1790, 1725, 1521, 1345, and 1172 cm$^{-1}$; UV (CH$_2$Cl$_2$) 272 nm; NMR (CDCl$_3$) δ 2.40 (s, 3, ArCH$_3$), 3.06 (dd, 1, J=3.0 and 17.2, H6β), 3.16 (dd, 1, J=9.0 and 9.0, H4a), 3.31 (dd, 1, J=9.0 and 10.0, H4b), 3.59 (dd, 1, J=5.8 and 17.2, H6α), 4.24 (m, I, H5), 5.20 and 5.32 (ABq, 2, J=14.0, CH$_2$Ar), 7.32 and 7.77 (two d's, 4, J=8.0, p-MeC$_6$H$_4$), 7.51 and 8.19 (two d's, 4, J=8.0, p-NO$_2$C$_6$H$_4$).

EXAMPLE 35

Benzyl 3-methoxy-1-azabicyclo[3.2.0]hept-2-en-7-one-2-carboxylate

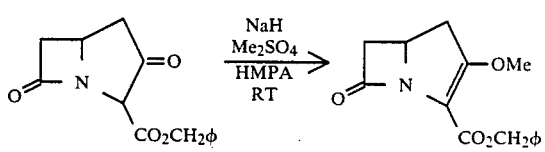

A solution of benzyl 1-azabicyclo[3.2.0]heptan-3,7-dione-2-carboxylate (25.9 mg, 0.1 mMol) in anhydrous hexamethylphosphoramide (1.0 ml) is cooled in an ice-bath and stirred under a nitrogen atmosphere. Dimethyl sulfate (11.4 μl, 0.12 mMol) and 57% sodium hydride in mineral oil (5.0 mg, 0.12 mMol) are added to the solution. The cooling bath is removed and the resulting mixture is stirred at room temperature for 60 minutes. The mixture is diluted with ethyl acetate (10 ml) and water (20 ml), shaken, and the layers separated. The organic layer is washed with water (3×5 ml) and brine, dried with magnesium sulfate, diluted with toluene (10 ml), and evaporated under vacuum to an oil. This material is chromatographed on a 0.25 mm×10×20 cm silica gel GF plate using 3:1 toluene-ethyl acetate as developing solvent. The major UV visible band at R$_f$0.1 was removed and eluted with ethyl acetate to provide benzyl 3-methoxy-1-azabicyclo[3.2.0]hept-2-en-7-one-2-carboxylate (5.6 mg) as a clear oil: IR (CH$_2$Cl$_2$) 1775 and 1700 cm$^{-1}$; UV (EtOAc) 288 nm; NMR (CDCl$_3$) δ 2.87 (dd, 1, J=2.8 and 16, H6β), 3.03 (m, 2, H4a and H4b), 3.50 (dd, 1, J=5.5 and 16, H6α), 3.80 (m, 1, H5), 3.92 (s, 3, CH$_3$), 5.28 (s, 2, CH$_2$φ), and 7.40 (m, 5, C$_6$H$_5$); mass spectrum m/e 273 (M+) and 231 (M+-42).

This product is also obtained by treating the bicyclo keto ester with dimethyl sulfate and excess potassium carbonate in hexamethylphosphoramide or dimethylformamide.

EXAMPLE 36

Benzyl 3-phenylthio-1-azabicyclo[3.2.0]hept-2en-7-one-2-carboxylate

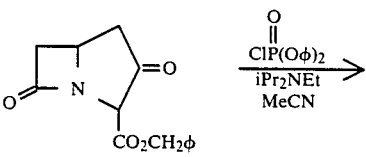

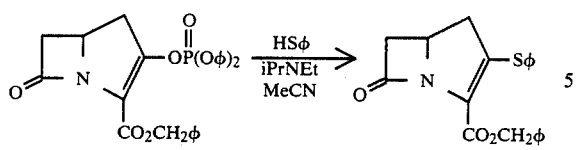 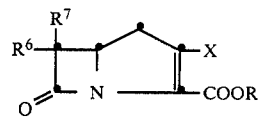

An ice-cold solution of benzyl 1-azabicyclo[3.2.0-]heptan-3,7-dione-2-carboxylate (13 mg, 0.05 mmol) in anhydrous acetonitrile is treated with N,N-diisopropylethylamine (10.4 μl, 0.06 mmol) and diphenyl chlorophosphate (10.9 μl, 0.053 mmol) and the resulting solution is stirred in the cold and under a nitrogen atmosphere for 90 mins. More N,N-diisopropylethylamine (8.7 μl, 0.05 mmol) and thiophenol (5.1 μl, 0.05 mmol) are added and the reaction mixture is stirred in the cold for 2 hours. The resulting mixture is combined with a second similar run, diluted with ethyl acetate to 10 ml volume, washed with water, 1M pH3 phosphate buffer, 5% aqueous sodium bicarbonate, and brine, dried over magnesium sulfate, and evaporated under vacuum to an oil (34 mg). This material is purified on a 0.25 mm×20×20 silica gel GF plate using 3:1 toluene-ethyl acetate as developing solvent. The UV visible band at $R_f$ 0.55 is removed and eluted with ethyl acetate. Evaporation of the solvent leaves a residue which is lyophilized from benzene to provide benzyl 3-phenylthio-1-azabicyclo[3.2.0]hept-2-en-7-one-2-carboxylate (17 mg) as an amorphous, white powder.

What is claimed is:

1. A process for preparing a compound having the structure:

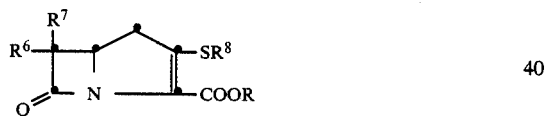

and the pharmaceutically acceptable salts thereof wherein R is H; pharmaceutically acceptable salt cation; or a pharmaceutically acceptable ester moiety; and $R^6$, $R^7$ and $R^8$ are independently selected from the group consisting of hydrogen, substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; phenyl; aralkyl, aralkenyl, and aralkynyl wherein the aryl moiety is phenyl and the linear chain has 1–6 carbon atoms; heteroaryl, heteroaralkyl, heterocyclyl and heterocyclylalkyl wherein the substituent or substituents relative to the above-named radicals are selected from the group consisting of: amino, mono-, di- and trialkylamino, hydroxyl, alkoxy, mercapto, alkylthio, phenylthio, sulfamoyl, amidino, guanidino, nitro, chloro, bromo, fluoro, cyano and carboxy; and wherein the hetero atom or atoms in the above-named heterocyclic moieties are selected from the group consisting of 1–4 oxygen, nitrogen or sulphur atoms; and wherein the alkyl moieties of the above-recited substituents have 1–6 carbon atoms; comprising treating:

with HSR$^8$ reagent calculated to provide the substituent —SR$^8$; wherein X is a leaving group; when R$^6$/R$^7$ is hydrogen R$^7$/R$^6$ is not 1-hydroxyethyl.

2. The process of claim 1 wherein: R$^6$ is hydrogen or methyl and R$^8$ is selected from the group consisting of:

H,
CH$_3$,
C(CH$_3$)$_2$CH$_2$NH$_2$,

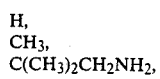

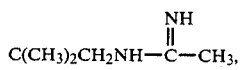

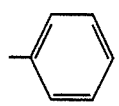

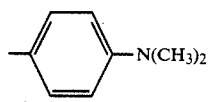

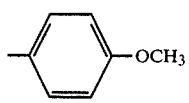

CH$_2$CH$_2$CH$_2$NH$_2$,
CH$_2$CH(CH$_3$)NH$_2$,

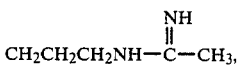

CH$_2$CH$_2$CH$_3$
CH$_2$CH$_2$N(CH$_3$)$_2$

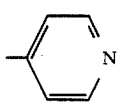

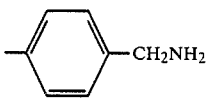

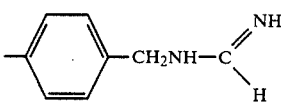

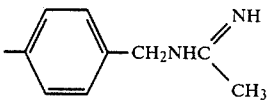

-continued

[benzyl structure] CH₂NH₂

[benzyl structure] CH₂NH—C(=NH)H

[benzyl structure] CH₂NHC(=NH)—CH₃

—CH₂—[phenyl]

[thiadiazole ring with CH₃ substituents]

[methyl-triazole with N-CH₃]

CH(CH₃)CH₂NH₂,

CH(CH₃)CH₂NH—C(=NH)—H,

CH(CH₃)CH₂NH—C(=NH)—CH₃

CH₃,
CH₃CH₂,
CH₃(CH₂)₂,
(CH₃)₂CH,
CH₃(CH₂)₃,
(CH₃)₂CH(CH₂)₂,
CH₂=CHCH₂,
CH≡CCH₂,

[cyclohexyl],

φ(CH₂)₃ (φ = PHENYL),
φ(CH₂)₂,
HO(CH₂)₂,
H₂N(CH₂)₂,
H₂N(CH₂)₃,
CH₃(CH₂)₂NH(CH₂)₂,

-continued

[cyclohexyl]—NH(CH₂)₂, (CH₃)₂N(CH₂)₂,
(CH₃CH₂)₂N(CH₂)₂,
HO₂C(CH₂)₂,
φCH₂,

[phenyl with (X)ₙ substituent]—  (n = 0, 1 or 2; X = Cl, Br, F, Cl, OCH₃, CH₃NH₂, NHC(=O)CH₃),

[thiadiazole with two CH₃ groups, N—N, S]

[tetrazole with CH₃]

[benzoxazole/benzothiazole Y—[ring]—X]  (when X = N, O, S, Y = H; when X = S, Y = H, OCH₂CH₃, Cl)

[2-pyridyl]

[4-pyridyl]

[quinoline, 2-position]

[thiazole, 2-position]

[furan, 2-position]

[imidazole with HN]

and R⁷ is selected from:

—CH₂OH

CH₃CH(OH)—

-continued
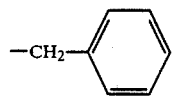
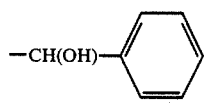
-continued
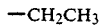
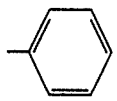
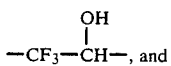
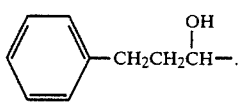
3. The process of claim 2 wherein X is chloro, bromo, toluene sulfonyloxy, p-nitrophenylsulfonyloxy, methyl sulfonyloxy, diphenylphosphoryl.
* * * * *